(12) United States Patent
White et al.

(10) Patent No.: US 8,771,230 B2
(45) Date of Patent: Jul. 8, 2014

(54) INTEGRATED VASCULAR DELIVERY SYSTEM

(75) Inventors: Steven B. White, Ann Arbor, MI (US); Adrienne Rose Harris, Tecumseh, MI (US); Elyse Kemmerer, Ann Arbor, MI (US); Nathan Farrell, Ann Arbor, MI (US); Ronald Dean Duis, Plainwell, MI (US); Henry J. H. Brown, Ann Arbor, MI (US)

(73) Assignee: Tangent Medical Technologies, LLC, Ann Arbor, MI (US)

( * ) Notice: Subject to any disclaimer, the term of this patent is extended or adjusted under 35 U.S.C. 154(b) by 237 days.

(21) Appl. No.: 13/111,693

(22) Filed: May 19, 2011

(65) Prior Publication Data
US 2011/0301541 A1 Dec. 8, 2011

Related U.S. Application Data

(60) Provisional application No. 61/356,776, filed on Jun. 21, 2010, provisional application No. 61/346,292, filed on May 19, 2010, provisional application No. 61/407,797, filed on Oct. 28, 2010, provisional application No. 61/418,349, filed on Nov. 20, 2010, provisional application No. 61/438,774, filed on Feb. 2, 2011, provisional application No. 61/418,358, filed on Nov. 30, 2010, provisional application No. 61/438,782, filed on Feb. 2, 2011, provisional application No. 61/448,318, filed on Mar. 2, 2011.

(51) Int. Cl.
*A61M 5/32* (2006.01)
*A61M 25/02* (2006.01)
*A61M 25/06* (2006.01)
*A61M 5/158* (2006.01)

(52) U.S. Cl.
CPC ........... *A61M 25/02* (2013.01); *A61M 25/0637* (2013.01); *A61M 5/158* (2013.01); *A61M 25/0631* (2013.01); *A61M 2025/024* (2013.01)
USPC ....................... 604/174; 604/164.04; 604/177

(58) Field of Classification Search
CPC ............ A61M 25/02; A61M 25/0637; A61M 2025/024; A61M 5/158; A61M 25/0631
USPC .................... 604/48, 164.02–164.04, 167.02, 604/174–177, 179, 180, 506, 513, 905
See application file for complete search history.

(56) References Cited

U.S. PATENT DOCUMENTS

| 2,868,200 | A | | 1/1959 | Gewecke | |
|---|---|---|---|---|---|
| 4,316,461 | A | * | 2/1982 | Marais et al. | ................. 604/179 |

(Continued)

FOREIGN PATENT DOCUMENTS

| CN | 101466431 A | 6/2009 |
|---|---|---|
| JP | 2910915 B2 | 6/1999 |

(Continued)

*Primary Examiner* — Nicholas Lucchesi
*Assistant Examiner* — Gerald Landry, II
(74) *Attorney, Agent, or Firm* — Jeffrey Schox

(57) ABSTRACT

An integrated vascular delivery system and method of use, the system including: a frame having a catheter hub that provides a first anchoring point on the patient and receives a catheter insertable in the patient to transfer fluid at an insertion site, a stabilization hub that provides a second anchoring point on the patient, at least one lateral member extending between the catheter and stabilization hubs, and a fluidic channel. The frame operates in a folded configuration in which the hubs are coupleable and an unfolded configuration in which the anchoring points are distributed around the insertion site to anchor the frame to the patient, thereby stabilizing the catheter. In some embodiments, the system further includes a septum that helps prevent fluid leakage from the catheter hub, or a needle shield that covers the distal end of a needle used during catheter insertion.

53 Claims, 15 Drawing Sheets

(56) References Cited

U.S. PATENT DOCUMENTS

| | | | |
|---|---|---|---|
| 4,380,234 A * | 4/1983 | Kamen | 604/180 |
| 4,397,641 A | 8/1983 | Jacobs | |
| 4,424,833 A | 1/1984 | Spector et al. | |
| 4,436,519 A | 3/1984 | O'Neill | |
| 4,591,356 A | 5/1986 | Christie | |
| 4,695,274 A | 9/1987 | Fox | |
| 4,755,170 A | 7/1988 | Golden | |
| 4,798,594 A | 1/1989 | Hillstead | |
| 4,898,587 A * | 2/1990 | Mera | 604/174 |
| 4,909,798 A | 3/1990 | Fleischhacker et al. | |
| 4,935,010 A | 6/1990 | Cox et al. | |
| 4,964,854 A | 10/1990 | Luther | |
| 5,000,740 A | 3/1991 | Ducharme et al. | |
| 5,049,136 A | 9/1991 | Johnson | |
| 5,085,648 A | 2/1992 | Purdy et al. | |
| 5,116,324 A | 5/1992 | Brierley et al. | |
| 5,135,504 A | 8/1992 | Mclees | |
| 5,171,234 A | 12/1992 | Jepson et al. | |
| 5,199,948 A | 4/1993 | McPhee | |
| 5,201,717 A | 4/1993 | Wyatt et al. | |
| 5,211,634 A | 5/1993 | Vaillancourt | |
| 5,215,525 A | 6/1993 | Sturman | |
| 5,215,528 A | 6/1993 | Purdy et al. | |
| 5,215,537 A | 6/1993 | Lynn et al. | |
| 5,232,010 A | 8/1993 | Rozenblatt et al. | |
| 5,238,010 A | 8/1993 | Grabenkort et al. | |
| 5,295,970 A | 3/1994 | Clinton et al. | |
| 5,300,034 A | 4/1994 | Behnke et al. | |
| 5,314,411 A | 5/1994 | Bierman et al. | |
| 5,351,383 A | 10/1994 | Behnke et al. | |
| 5,354,275 A | 10/1994 | Behnke et al. | |
| 5,354,282 A | 10/1994 | Bierman | |
| 5,360,408 A | 11/1994 | Vaillancourt | |
| 5,364,368 A | 11/1994 | Kauffman et al. | |
| 5,368,801 A | 11/1994 | Vaillancourt | |
| 5,375,589 A | 12/1994 | Bhatta | |
| 5,400,500 A | 3/1995 | Behnke et al. | |
| 5,405,331 A | 4/1995 | Behnke et al. | |
| 5,413,562 A | 5/1995 | Swauger | |
| 5,425,721 A | 6/1995 | Malenchek | |
| 5,472,430 A | 12/1995 | Vaillancourt et al. | |
| 5,474,544 A | 12/1995 | Lynn | |
| 5,476,452 A | 12/1995 | Thompson | |
| 5,487,728 A | 1/1996 | Vaillancourt | |
| 5,487,734 A | 1/1996 | Thorne et al. | |
| 5,498,247 A | 3/1996 | Brimhall | |
| 5,509,912 A | 4/1996 | Vaillancourt et al. | |
| 5,514,116 A | 5/1996 | Vaillancourt et al. | |
| 5,522,804 A | 6/1996 | Lynn | |
| 5,549,651 A | 8/1996 | Lynn | |
| 5,558,651 A | 9/1996 | Crawford et al. | |
| 5,575,769 A | 11/1996 | Vaillancourt | |
| 5,591,138 A | 1/1997 | Vaillancourt | |
| 5,601,536 A | 2/1997 | Crawford et al. | |
| 5,643,216 A * | 7/1997 | White | 604/174 |
| 5,669,891 A | 9/1997 | Vaillancourt | |
| 5,676,656 A | 10/1997 | Brimhall | |
| 5,697,914 A | 12/1997 | Brimhall | |
| 5,697,915 A | 12/1997 | Lynn | |
| 5,702,371 A | 12/1997 | Bierman | |
| 5,727,770 A | 3/1998 | Dennis | |
| 5,735,827 A | 4/1998 | Adwers et al. | |
| 5,743,884 A | 4/1998 | Hasson et al. | |
| 5,746,727 A | 5/1998 | Graves et al. | |
| 5,749,857 A | 5/1998 | Cuppy | |
| 5,755,709 A | 5/1998 | Cuppy | |
| 5,769,825 A | 6/1998 | Lynn | |
| 5,788,675 A | 8/1998 | Mayer | |
| 5,810,780 A | 9/1998 | Brimhall et al. | |
| 5,830,184 A | 11/1998 | Basta | |
| 5,879,330 A | 3/1999 | Bell | |
| 5,902,274 A | 5/1999 | Yamamoto et al. | |
| 5,916,199 A | 6/1999 | Miles | |
| 5,935,110 A | 8/1999 | Brimhall | |
| 5,957,887 A | 9/1999 | Oesterlind et al. | |
| 5,997,504 A | 12/1999 | Bell | |
| 6,004,294 A | 12/1999 | Brimhall et al. | |
| 6,027,480 A | 2/2000 | Davis et al. | |
| 6,033,382 A | 3/2000 | Basta | |
| 6,056,718 A | 5/2000 | Funerburk et al. | |
| 6,086,564 A | 7/2000 | McLaughlin | |
| 6,142,981 A | 11/2000 | Heck et al. | |
| 6,149,632 A | 11/2000 | Landuyt | |
| 6,162,206 A | 12/2000 | Bindokas et al. | |
| 6,171,287 B1 | 1/2001 | Lynn et al. | |
| 6,197,007 B1 * | 3/2001 | Thorne et al. | 604/263 |
| 6,210,624 B1 | 4/2001 | Mayer | |
| 6,228,065 B1 | 5/2001 | Lynn | |
| 6,261,259 B1 | 7/2001 | Bell | |
| 6,261,268 B1 | 7/2001 | Mayer | |
| 6,273,869 B1 | 8/2001 | Vaillancourt | |
| 6,273,871 B1 | 8/2001 | Davis et al. | |
| RE37,357 E | 9/2001 | Lynn | |
| 6,342,120 B1 | 1/2002 | Basta | |
| 6,375,639 B1 | 4/2002 | Duplessie et al. | |
| 6,379,333 B1 | 4/2002 | Brimhall et al. | |
| 6,379,337 B1 | 4/2002 | Mohammad | |
| 6,506,181 B2 | 1/2003 | Meng et al. | |
| 6,520,938 B1 | 2/2003 | Funderburk et al. | |
| 6,569,120 B1 | 5/2003 | Green et al. | |
| RE38,145 E | 6/2003 | Lynn | |
| 6,572,588 B1 | 6/2003 | Bierman | |
| 6,572,591 B2 | 6/2003 | Mayer | |
| 6,595,955 B2 | 7/2003 | Ferguson et al. | |
| 6,623,461 B1 | 9/2003 | Wilkinson et al. | |
| 6,638,252 B2 | 10/2003 | Moulton et al. | |
| 6,652,490 B2 | 11/2003 | Howell | |
| 6,663,599 B2 | 12/2003 | Osbourne et al. | |
| 6,673,046 B2 | 1/2004 | Bierman et al. | |
| 6,699,221 B2 | 3/2004 | Vaillancourt | |
| 6,719,726 B2 | 4/2004 | Meng et al. | |
| 6,719,727 B2 | 4/2004 | Brimhall et al. | |
| 6,730,096 B2 | 5/2004 | Basta | |
| 6,740,277 B2 | 5/2004 | Howell et al. | |
| 6,749,588 B1 | 6/2004 | Howell et al. | |
| 6,761,706 B2 | 7/2004 | Vaillancourt | |
| 6,776,775 B1 | 8/2004 | Mohammad | |
| 6,805,860 B1 | 10/2004 | Alt | |
| 6,811,545 B2 | 11/2004 | Vaillancourt | |
| 6,837,875 B1 | 1/2005 | Bierman | |
| 6,902,546 B2 | 6/2005 | Ferguson | |
| 6,905,483 B2 | 6/2005 | Newby et al. | |
| 6,908,459 B2 | 6/2005 | Harding et al. | |
| 6,926,721 B2 | 8/2005 | Basta | |
| 6,953,448 B2 | 10/2005 | Moulton et al. | |
| 6,955,659 B1 | 10/2005 | Carter | |
| 6,972,002 B2 | 12/2005 | Thorne | |
| 6,981,965 B2 | 1/2006 | Luther et al. | |
| 6,981,966 B2 | 1/2006 | Green et al. | |
| 6,984,223 B2 | 1/2006 | Newby et al. | |
| RE38,996 E | 2/2006 | Crawford et al. | |
| 6,997,902 B2 | 2/2006 | Thorne et al. | |
| 6,997,913 B2 | 2/2006 | Wilkinson | |
| 7,004,934 B2 | 2/2006 | Vaillancourt | |
| 7,008,406 B2 | 3/2006 | Mayer | |
| 7,022,111 B2 | 4/2006 | Duplessie et al. | |
| 7,033,339 B1 | 4/2006 | Lynn | |
| 7,060,055 B2 | 6/2006 | Wilkinson et al. | |
| 7,060,060 B1 | 6/2006 | Simpson et al. | |
| 7,090,660 B2 | 8/2006 | Roberts et al. | |
| 7,090,661 B2 | 8/2006 | Morris et al. | |
| RE39,334 E | 10/2006 | Lynn | |
| 7,125,398 B2 | 10/2006 | Garcia, Jr. | |
| 7,220,249 B2 | 5/2007 | Hwang et al. | |
| 7,258,680 B2 | 8/2007 | Mogensen et al. | |
| 7,344,516 B2 | 3/2008 | Erskine | |
| 7,347,842 B2 | 3/2008 | Thorne et al. | |
| 7,351,230 B2 | 4/2008 | Smith et al. | |
| 7,354,422 B2 | 4/2008 | Riesenberger et al. | |
| 7,413,562 B2 | 8/2008 | Ferguson et al. | |
| 7,435,238 B2 | 10/2008 | Reid | |
| 7,445,611 B2 | 11/2008 | Osborne et al. | |
| 7,470,261 B2 | 12/2008 | Lynn | |
| 7,507,222 B2 | 3/2009 | Cindrich et al. | |

(56) References Cited

U.S. PATENT DOCUMENTS

| | | |
|---|---|---|
| 7,604,616 B2 | 10/2009 | Thoresen et al. |
| 7,615,033 B2 | 11/2009 | Leong |
| 7,618,395 B2 | 11/2009 | Ferguson |
| 7,635,357 B2 | 12/2009 | Mayer |
| 7,651,481 B2 | 1/2010 | Raybuck |
| 7,658,725 B2 | 2/2010 | Bialecki et al. |
| 7,670,317 B2 | 3/2010 | Cindrich et al. |
| 7,699,814 B2 | 4/2010 | Lande |
| 7,713,243 B2 | 5/2010 | Hillman |
| 7,713,250 B2 | 5/2010 | Harding et al. |
| 7,717,882 B2 | 5/2010 | Harding |
| 7,722,569 B2 | 5/2010 | Soederholm et al. |
| 7,736,332 B2 | 6/2010 | Carlyon et al. |
| 7,736,337 B2 | 6/2010 | Diep et al. |
| 7,744,572 B2 | 6/2010 | Bierman |
| 7,749,254 B2 | 7/2010 | Sobelman et al. |
| 7,763,199 B2 | 7/2010 | Fangrow, Jr. |
| 7,766,879 B2 | 8/2010 | Tan et al. |
| 7,771,412 B2 | 8/2010 | Anderson et al. |
| 7,776,017 B2 | 8/2010 | Ponzi et al. |
| 7,798,991 B2 | 9/2010 | Insignares |
| 7,798,994 B2 | 9/2010 | Brimhall |
| 7,799,000 B2 | 9/2010 | Silich |
| 7,833,201 B2 | 11/2010 | Carlyon et al. |
| 7,862,547 B2 | 1/2011 | Ferguson et al. |
| 7,887,515 B2 | 2/2011 | Bierman |
| 7,918,828 B2 | 4/2011 | Lundgaard et al. |
| 7,959,613 B2 | 6/2011 | Rhad et al. |
| 8,012,145 B2 | 9/2011 | Cawley |
| 8,025,644 B2 | 9/2011 | Chong et al. |
| 8,062,262 B2 | 11/2011 | Christensen et al. |
| 8,066,669 B2 | 11/2011 | Christensen et al. |
| 8,066,675 B2 | 11/2011 | Cindrich et al. |
| 8,066,678 B2 | 11/2011 | Vaillancourt et al. |
| 8,070,725 B2 | 12/2011 | Christensen |
| 8,083,728 B2 | 12/2011 | Rome |
| 8,092,435 B2 | 1/2012 | Beling et al. |
| 8,123,738 B2 | 2/2012 | Vaillancourt |
| 8,133,202 B2 | 3/2012 | Marsh |
| 8,147,455 B2 | 4/2012 | Butts et al. |
| 8,147,465 B2 | 4/2012 | Kern |
| 8,157,770 B2 | 4/2012 | Elwell et al. |
| 8,162,882 B2 | 4/2012 | Rubinstein et al. |
| 8,162,896 B2 | 4/2012 | Tan |
| 8,163,237 B2 | 4/2012 | Crawford et al. |
| 8,172,803 B2 | 5/2012 | Morrissey et al. |
| 8,177,745 B2 | 5/2012 | Brechbuehler et al. |
| 8,177,753 B2 | 5/2012 | Vitullo et al. |
| 8,177,754 B2 | 5/2012 | Barnes |
| 8,177,755 B2 | 5/2012 | Berry et al. |
| 8,177,762 B2 | 5/2012 | Beasley et al. |
| 8,177,772 B2 | 5/2012 | Christensen et al. |
| 2003/0083620 A1 | 5/2003 | Luther et al. |
| 2003/0199827 A1 | 10/2003 | Thorne |
| 2004/0010227 A1 | 1/2004 | Riesenberger et al. |
| 2004/0181192 A1 | 9/2004 | Cuppy |
| 2004/0267210 A1 | 12/2004 | Popovsky |
| 2006/0094983 A1 | 5/2006 | Burbank et al. |
| 2006/0155258 A1 | 7/2006 | Rogers et al. |
| 2006/0189942 A1 | 8/2006 | Chang et al. |
| 2006/0270994 A1 | 11/2006 | Bierman |
| 2007/0142785 A1 | 6/2007 | Lundgaard et al. |
| 2007/0161950 A1 | 7/2007 | Carlyon et al. |
| 2007/0173768 A2 | 7/2007 | Bierman |
| 2007/0270754 A1 | 11/2007 | Soderholm et al. |
| 2008/0147009 A1 | 6/2008 | Nilsson et al. |
| 2008/0195033 A1 | 8/2008 | Eagleson et al. |
| 2009/0036836 A1 | 2/2009 | Nystrom et al. |
| 2009/0043260 A1 | 2/2009 | Bierman |
| 2009/0137958 A1 | 5/2009 | Erskine |
| 2009/0137961 A1 | 5/2009 | Bracken |
| 2009/0227896 A1 | 9/2009 | Alvin Tan et al. |
| 2010/0234804 A1* | 9/2010 | Hiejima et al. ............... 604/110 |
| 2010/0262038 A1 | 10/2010 | Tan et al. |
| 2010/0262083 A1 | 10/2010 | Grunhut et al. |
| 2010/0274199 A1 | 10/2010 | Weston |
| 2010/0286623 A1 | 11/2010 | Liversidge |
| 2011/0015573 A1 | 1/2011 | Maan et al. |
| 2011/0060288 A1 | 3/2011 | Carlyon et al. |
| 2011/0125096 A1 | 5/2011 | Baid |
| 2011/0178427 A1 | 7/2011 | Tan et al. |
| 2011/0178464 A1 | 7/2011 | Rawls |
| 2011/0178478 A1* | 7/2011 | Huet et al. ............... 604/288.04 |
| 2011/0208124 A1 | 8/2011 | Rhad et al. |
| 2012/0041377 A1 | 2/2012 | Haak |
| 2012/0065612 A1 | 3/2012 | Stout et al. |
| 2012/0150121 A1 | 6/2012 | Silverman et al. |

FOREIGN PATENT DOCUMENTS

| | | |
|---|---|---|
| JP | 4211858 B2 | 1/2009 |
| WO | 2006082350 A | 8/2006 |

* cited by examiner

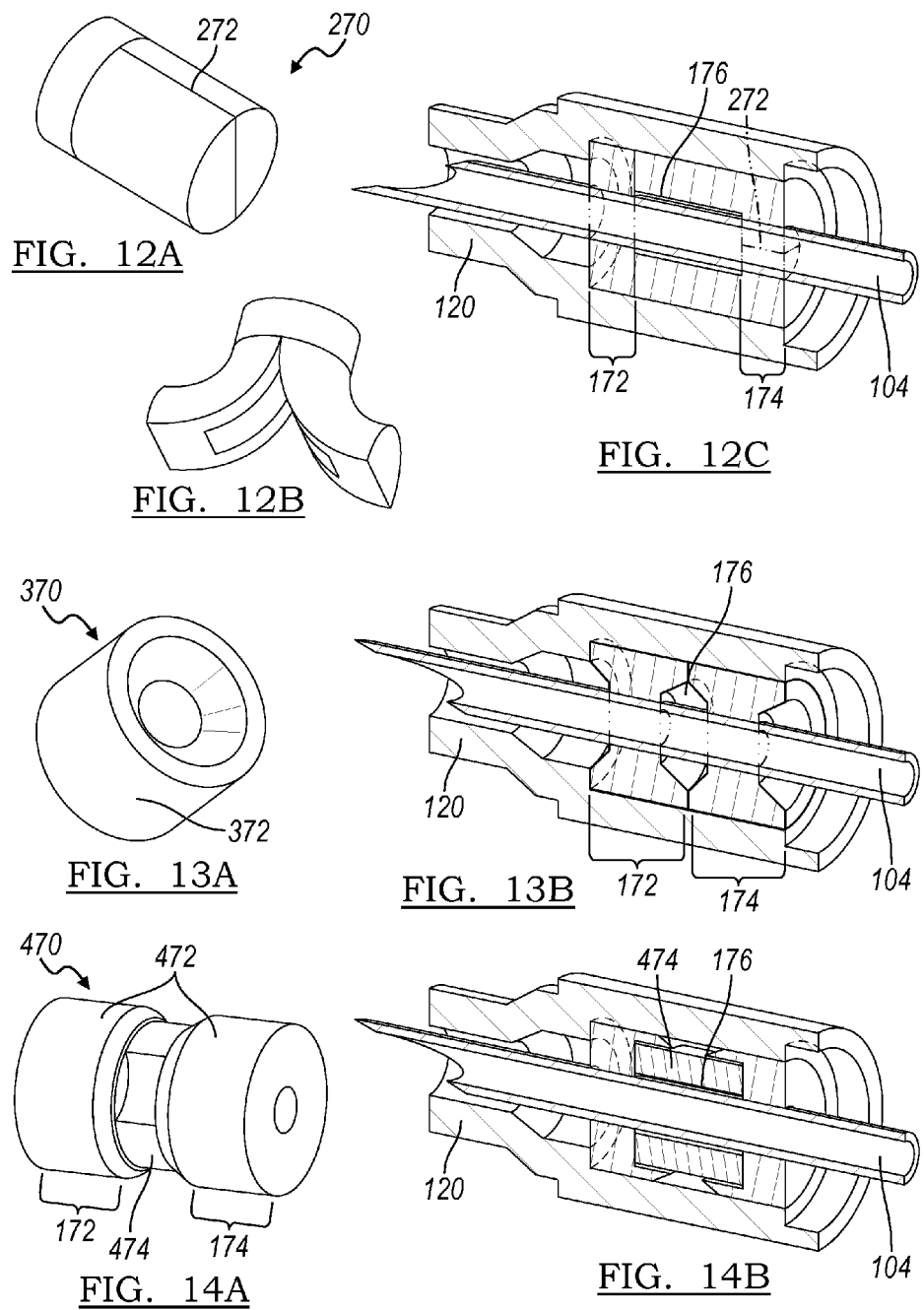

INTEGRATED VASCULAR DELIVERY SYSTEM

CROSS-REFERENCE TO RELATED APPLICATIONS

This application claims the benefit of U.S. Provisional Application No. 61/356,776 filed 21 JUN. 2010. This application also claims the benefit of U.S. Provisional Application Nos. 61/346,292 filed 19 MAY 2010 and 61/407,797 filed 28 OCT. 2010. This application also claims the benefit of U.S. Provisional Application Nos. 61/418,349 filed 20 NOV. 2010 and 61/438,774 filed 2 FEB. 2011. This application also claims the benefit of U.S. Provisional Application Nos. 61/418,358 filed 30 NOV. 2010, 61/438,782 filed 2 FEB. 2011, and 61/448,318 filed 2 MAR. 2011. All eight provisional applications are each incorporated in its entirety by this reference.

TECHNICAL FIELD

This invention relates generally to the medical care field, and more specifically to an improved vascular delivery system in the intravenous therapy field.

BACKGROUND

Patients undergoing medical treatment often require a form of intravenous (IV) therapy, in which a fluid is administered to the patient through a vein of the patient. IV therapy is among the fastest ways to deliver fluids and medications into the body of the patient. Intravenously infused fluids, which typically include saline, drugs, blood, and/or antibiotics, are conventionally introduced to the patient through a flexible catheter positioned at any of several venous routes, such as peripheral veins and central veins.

To set up IV therapy with conventional devices and methods, the caregiver positions the catheter over the selected vein and uses a needle within the catheter to pierce the skin and allow insertion of the distal end of the catheter into the vein. The proximal end of the catheter, relative to the midline of the catheter, is fixed to the end of a catheter hub that is proximal relative to the midline of the patient. The caregiver connects the catheter to a fluid supply through external tubing, including extension tubing that is typically attached to the catheter hub and that the caregiver typically bends into a U-shape to accommodate the typical opposite positions of the catheter and IV fluid source. To avoid unscheduled IV line restarts, the catheter and tubing are typically secured against the skin of the patient with tape or similar catheter stabilization devices (CSDs) such as adhesive stabilizing pads that restrain the catheter hub.

However, these conventional devices and methods for IV therapy have drawbacks. The extension tubing may catch on nearby obstacles during patient movement or caregiver manipulation, which may cause painful vein irritation and comprise the IV. Tape and other existing CSDs are not optimal for stabilization because securing the round, rigid, and bulky components such as the catheter and tubing against relative flat skin can be difficult and ineffective. Tape and other existing CSDs do not fully prevent the catheter from moving within the vein, which leads to patient-endangering complications including catheter dislodgement, infiltration (fluid entering surrounding tissue instead of the vein) and phlebitis (inflammation of the vein). Adhesive stabilizing pads tend to result in other undesired effects, such as skin irritation and/or breakdown due to prolonged concentrated adhesion to the skin. Furthermore, tape and current CSDs do not prevent the catheter from painfully and dangerously pivoting around the insertion site and moving within the vein.

Thus, there is a need in the medical care field to create an improved vascular delivery system. This invention provides such an improved vascular delivery system.

BRIEF DESCRIPTION OF THE FIGURES

FIGS. 11-17 are schematics of variations of the septum in the integrated vascular delivery system of a preferred embodiment;

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1A:
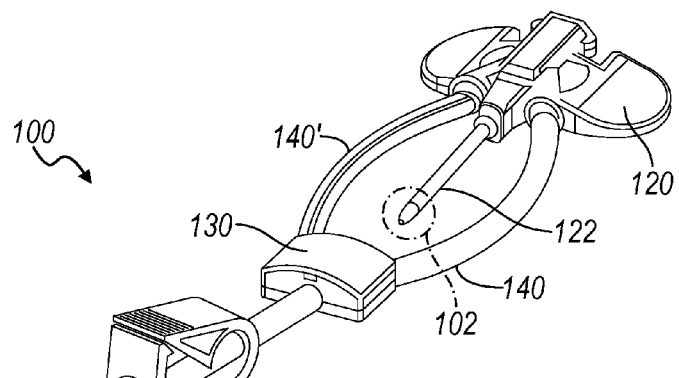
FIGS. 1-3 are schematics of the integrated vascular delivery system of a preferred embodiment.
Figure 1B:
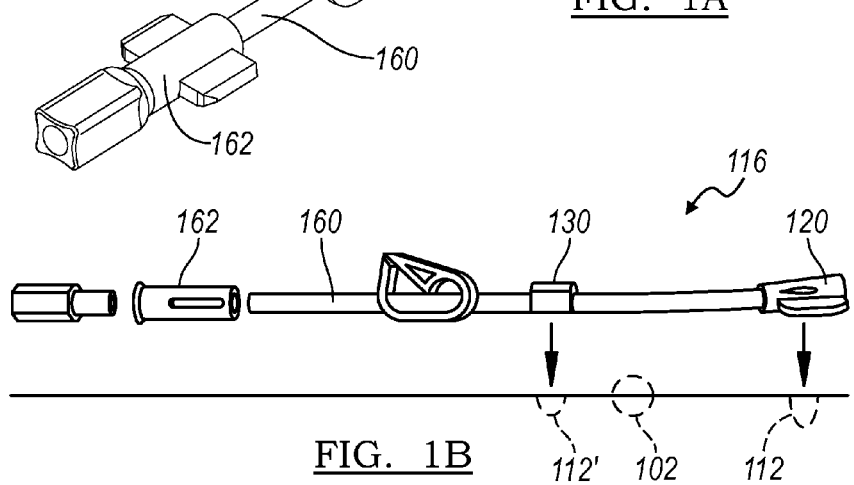
Figure 2:
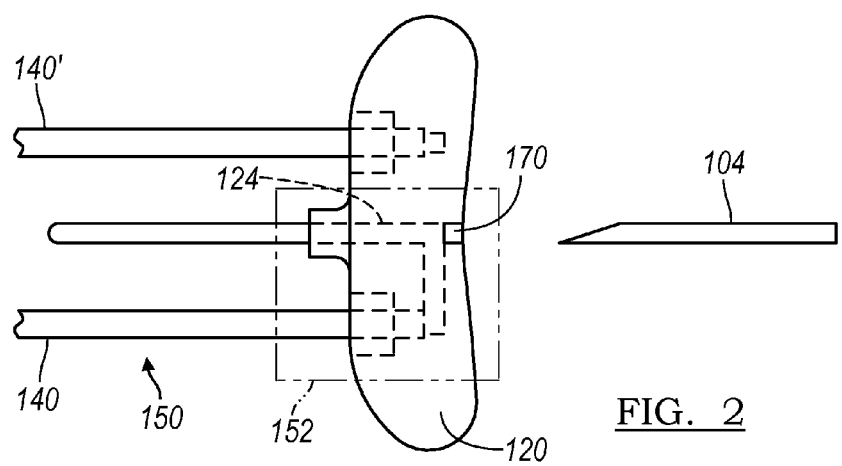
Figure 3:
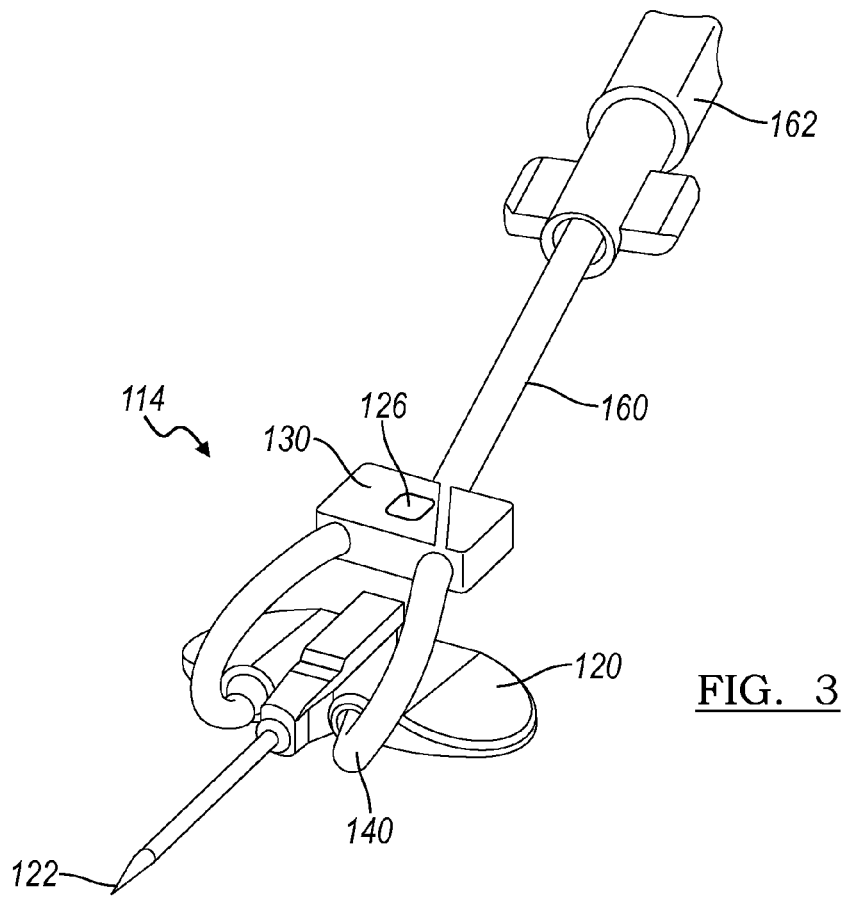

As shown in FIGS. 1-3, the integrated vascular delivery system 100 of a preferred embodiment includes: a frame 110 having a catheter hub 120 configured to receive a catheter 122, a stabilization hub 130, and at least one lateral member 140 extending between the catheter hub and stabilization hub; and a fluidic channel 150 that fluidically communicates with the catheter. The catheter hub 120 preferably provides a first anchoring point 112 on the patient and is configured to receive a catheter 122 insertable in a patient to transfer fluid at an insertion site 102, and the stabilization hub 130 preferably provides a second anchoring point 112' on the patient. The frame 110 preferably operates in a folded configuration 114 in which the catheter and stabilization hubs may be coupled, and in an unfolded configuration 116 in which the first and second anchoring points are distributed around the insertion site 102 to anchor the frame 110 to the patient, thereby stabilizing the catheter. For instance, in a preferred embodiment the first and second anchoring points are on opposite sides of the insertion site, such as proximal and distal to the side, or on opposite lateral sides of the insertion site. The system 100 preferably includes a catheter 122, such as a catheter embedded in the catheter hub 120, but may the system may alternatively be configured to receive and/or couple to a separate catheter before or after insertion into the patient. In some embodiments, the system may further include a septum 170 that helps prevent escape or leakage of fluids from the fluidic channel 150. In some embodiments, the system may further include a needle shield 190, coupled to the catheter hub and/or stabilization hub, that engages a distal portion of a needle 104 used for inserting the catheter 122 into the patient. The system may be used to obtain access to a blood vessel of a patient, such as one undergoing intravenous (IV) therapy. The system may be used to administer drugs, antibiotics, saline, blood, or any suitable fluid to a patient, and/or to remove fluid from the patient. The system may be used to create, stabilize, and maintain an IV line at an insertion site on a peripheral vein or artery such as on the arm, hand, or leg, or for central venous access on the neck, chest, abdomen, or any suitable IV location. However, the system may be used to create, stabilize, and maintain any suitable catheter-based access to a patient, such as catheters for transfer of cerebrospinal fluid.

Integrated Vascular Delivery System—Frame and Fluidic Channel

The frame 110 of the integrated vascular delivery system functions to stabilize the system and the catheter on the patient. As shown in FIGS. 1-3, the frame 110 preferably includes a catheter hub 120 that provides a first anchoring point 112 on the patient, a stabilization hub 130 that provides a second anchoring point 112' on the patient, and at least one lateral member 140 that extends between the catheter and the stabilization hubs. In alternative embodiments of the frame 110, the frame may include any suitable number of hubs and any suitable number of lateral members, such that the frame forms an enclosed or partial, non-enclosed perimeter of any suitable shape and size around the insertion site 102. The frame preferably allows visualization of the insertion site of the catheter, such as by leaving an open uncovered area around the catheter, although alternatively the system may include a cover that is transparent, translucent, opaque, or any suitable kind of materials, that extends over the frame to cover the insertion site and/or catheter.

The catheter hub 120 is configured to receive a catheter 122, which may be embedded in the catheter hub and integrally part of the system, or may be a separate catheter that is coupled to the catheter hub 120 before or after insertion into the patient, such as with a snap fit into the catheter hub 120. Alternatively, any suitable portion of the frame may be configured to receive the catheter. The catheter hub 120 preferably includes a channel 124, concentrically aligned with the catheter, that may receive a needle 104 used during insertion of the catheter into the patient. As shown in FIG. 3, the catheter hub and/or stabilization hub may include a sensor 126 that measures a biometric parameter such as temperature, blood pressure, or pulse rate of the patient. The sensor 126 may additionally and/or alternatively sense any suitable parameter such as one pertaining to the fluid passing through the catheter, such as pH or flow rate.

The catheter hub and/or stabilization hub may have a relatively wide and thin profile, which may help distribute forces over a greater area on the skin and decreases the chances of the patient developing skin irritations, sores, and other degradations. The thin profile may help decrease the risk of the risk of the hub catching or snagging on bed equipment or other nearby obstacles that could cause the catheter to move within the vein and cause complications such as catheter dislodgement, infiltration, and phlebitis. However, the catheter and stabilization hubs may have any suitable shape. The catheter and stabilization hubs may include a rigid or semirigid plastic or other suitable material, and/or softer material. For example, one or both hubs may include a rigid core overmolded with a softer material such as silicone.

The system may further include at least one extension tube 160 and/or a fluid supply adapter 162, coupled to the catheter hub 120 and/or stabilization hub 130, that delivers fluid from a fluid supply to the fluidic channel 150. The extension tube 160, which provides stress relief if the system is jostled (such as from patient movement or caregiver manipulations), is preferably made of flexible tubing such as polymer tubing, but may alternatively be a passageway made of any other suitable material. The extension tube 160 is preferably long enough to provide stress relief if needed, but short enough to reduce the chances of the extension tube catching or snagging on nearby obstacles. In another variation, the fluidic channel 150 and/or extension tube 160 may be coiled like a spring to provide stress relief. The length of the extension tube may alternatively be any suitable length, and may depend on the specific application of the system. Other dimensions of the extension tube, such as outer diameter and inner diameter, may also depend on the specific application of the system. The fluid supply adapter 162 preferably includes a connector that attaches the extension tube to a fluid supply (e.g. pole-mounted IV bag, syringe, or pump that supplies fluid through tubing). The connector may be a standard female luer lock connector (FIGS. 5A and 5B) or Y-connector (FIGS. 5C and 5D) that commonly interfaces with conventional IV bags. Alternatively, the connector may be any suitable male or female connector that is adapted to interface with a fluid supply. Furthermore, the luer lock connector or other fluid supply adapter may be coupled directly to the catheter hub and/or stabilization hub, rather than to an extension tube.

In alternative versions of the system, the system may include more than one extension tube 160 and/or fluid supply adapter 162, to facilitate delivering fluid from multiple fluid supplies simultaneously to the system. For example, in an embodiment of the system that includes two fluidic channels, the system may include a first extension tube that delivers a first fluid to a first fluidic channel, and a second extension tube that delivers a second fluid to the second fluidic channel. However, two extension tubes may useful in applications involving the administering of two separate fluids through the same fluidic channel 150 and catheter.

Figure 4:
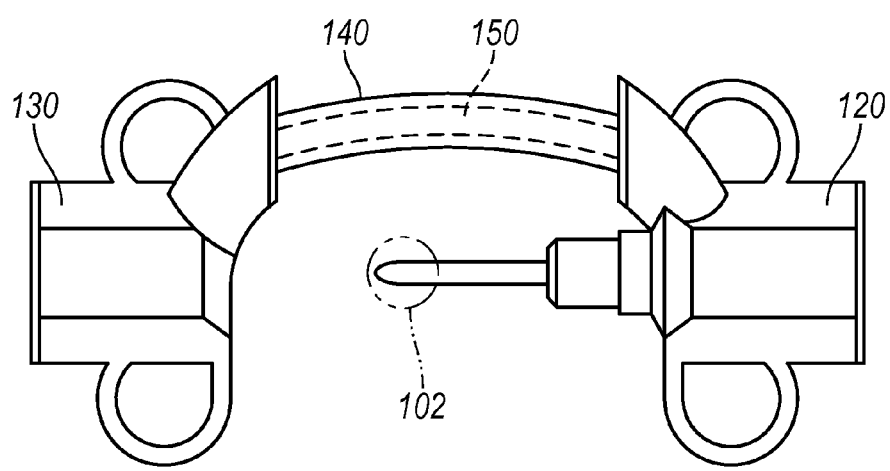
FIGS. 4-6 are schematics of variations of the integrated vascular delivery system.

The lateral member 140 functions to provide structural stability to the frame 110 by stabilizing the catheter hub 120 relative to the stabilization hub 130. As shown in FIGS. 1-3, the frame preferably includes two lateral members 140 and 140' that, with the catheter and stabilization hubs, form a perimeter around the catheter. The two lateral members may be approximately parallel, or may be in any crossed, non-parallel or other suitable orientation. However, as shown in FIG. 4, the frame 110 may include only a partial perimeter around the catheter, such as with one lateral member instead of two. Each lateral member 140 may be flexible, such as to allow the catheter and stabilization hubs to move relative to one another with a significant number of degrees of freedom, including displacement in the compression direction (and subsequent displacement in the tension direction) along the axis of the catheter, displacement in both directions along the other two axes, twisting in both directions along the axis of the catheter, and bending in both directions along the other two axes. In particular, the lateral member 140 may be reversibly bendable to allow the frame 110 to be in a folded configuration in which the catheter and stabilization hubs are coupleable. One or more lateral members may be tubular. For example, the lateral member may be a generally straight, soft, and flexible hollow channel like medical tubing, but may be any suitable structure with a lumen.

Figure 6A:
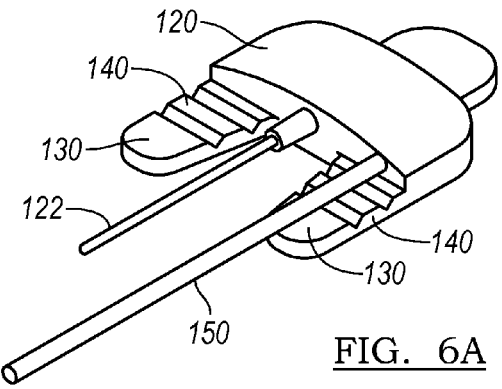
Figure 6B:
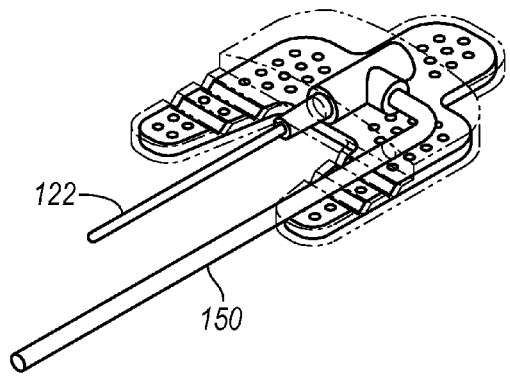
Figure 6C:
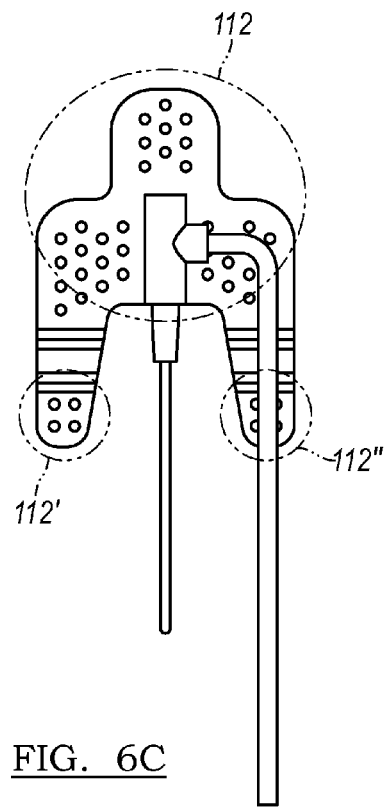
Figure 7A:
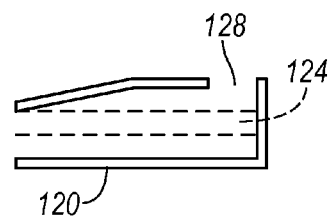
FIGS. 7-10 are schematics of variations of mechanisms for coupling the catheter hub and stabilization hub in the folded configuration of the integrated vascular delivery system of a preferred embodiment.
Figure 7B:
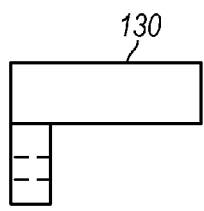
Figure 7C:
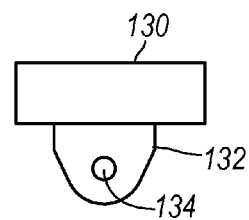
Figure 7D:
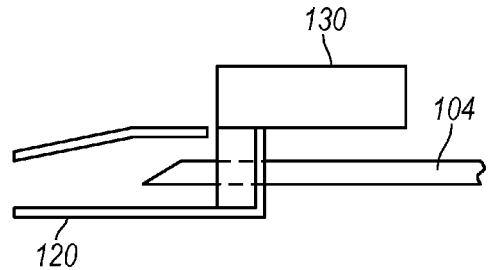

The fluidic channel 150 functions to deliver fluid from a fluid supply to the catheter, and in some embodiments, deliver fluid to and from the catheter, such as transferring fluid removed from the patient through the catheter to an external reservoir. As shown in FIG. 2, at least a portion of the fluidic channel 150 may be fixed within at least one of the hubs and/or within a tubular lateral member. As shown in FIGS. 6A-6C, at least a portion of the fluidic channel 150 may be additionally and/or alternatively be external to the hubs and lateral members. For instance, at least a portion of the fluidic channel 150 may be molded to an external surface of the catheter hub, the stabilization hub, and/or lateral member. The fluidic channel 150 preferably includes a turnabout portion 152 in which fluid flows in a direction different from that within the catheter 122. In particular, the turnabout portion 152 preferably directs the fluid flow to a direction opposite of that within the catheter, or in an approximately 180-degree turn. The turnabout portion 152 of the fluidic channel 150 may be fixed or embedded within the catheter hub and/or stabilization hub. In one exemplary application of the system, the catheter is inserted in the patient such that its penetrating end points proximally towards the heart of the patient, and the turnabout portion of the fluidic channel 150 allows a stand supporting the IV bag or other fluid supply to be kept near the head of a bed, or otherwise proximal to the insertion site as is typically practiced in patient treatment settings. The internalized fluid flow turn in the turnabout portion 152 of the fluidic channel 150 reduces the number of external structures that can get caught or snagged on nearby obstacles and consequently disturb the catheter and IV setup. Another effect of the turnabout portion is that if external tubing in the IV setup is pulled or caught, the turnabout portion may enable the frame 110 to stabilize the catheter more effectively by causing the catheter to be pulled further into the patient. For example, in a common catheter placement in which the catheter is placed on the forearm with its distal end pointing proximally toward the elbow of the patient, if the external tubing is accidentally pulled posteriorly towards the patient, the tubing will in turn pull the turnabout portion of the fluidic channel 150 and the catheter hub 120 toward the patient, thereby pulling the catheter further into the blood vessel of the patient rather than displacing the catheter from the insertion site.

Figure 5A:
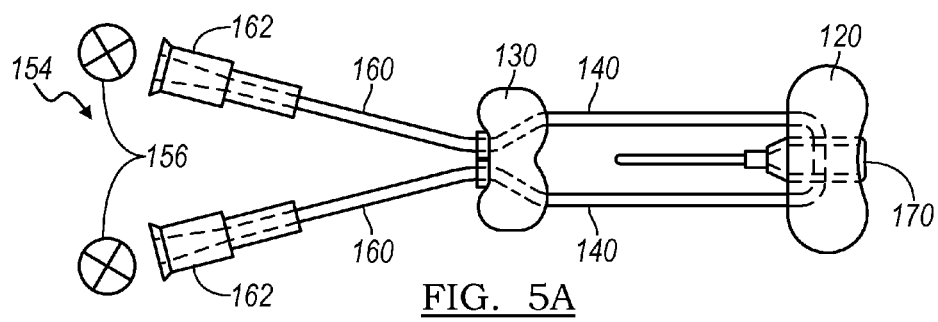
Figure 5B:
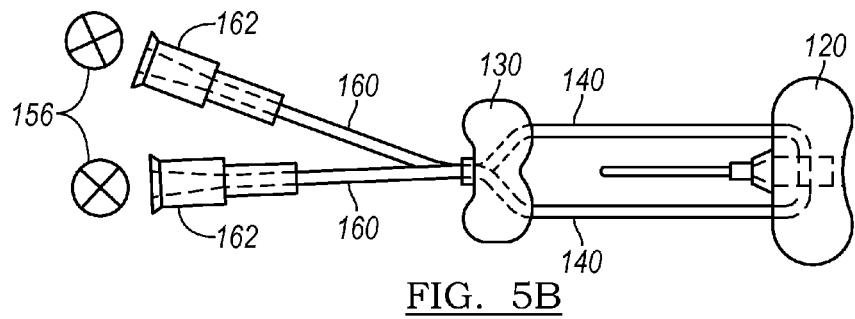
Figure 5C:
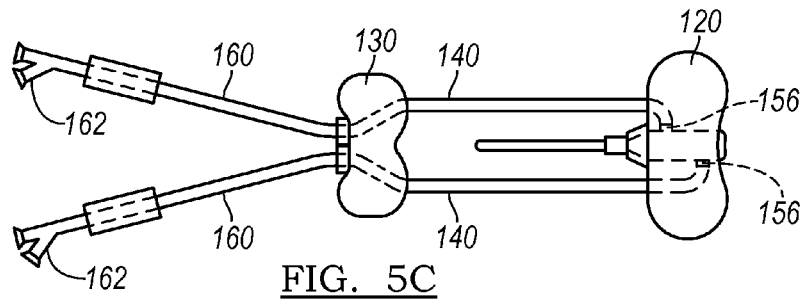
Figure 5D:
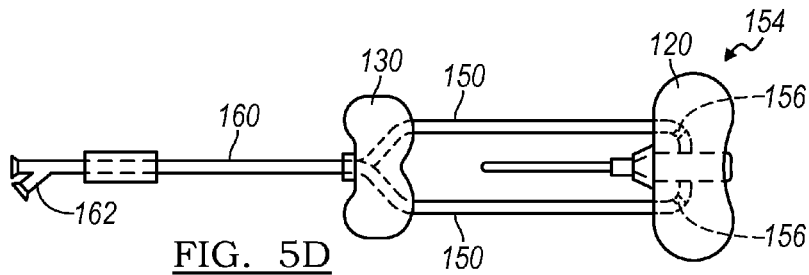

In some variations, the system may include one, two, or any suitable number of fluidic channels. For instance, a second fluidic channel 150 may pass through a second lateral member 140. The second fluidic channel 150 preferably receives a second fluid, which may be the same or different from the first fluid supplied to the first fluidic channel 150. As shown in FIGS. 5A-5C, the system may further include a second extension tube 160 that supplies a second fluid to the frame and catheter. However, as shown in FIG. 5D, the system may include only one extension tube 160 that supplies fluid to one or multiple fluidic channels. The fluidic channels may have separate inlets on the stabilization hub 130 (FIGS. 5A and 5C), or may share the same inlet on the stabilization hub in which flow may be regulated with valves or other fluid control means (FIGS. 5B and 5D). In one variation, the first and second fluidic channels preferably fluidically communicate with the same catheter in the catheter hub 120, coupled to the catheter at the same point (FIGS. 5A and 5B) or different points (FIG. 5C) along the length of the catheter or channel. In this variation, the system preferably includes a flow control system 154 that selectively restricts flow of one or both of the fluids to the catheter and therefore to the patient. The flow control system 154 may include one or more valves 156, such as at the extension tubes (FIGS. 5A and 5B), at the junction between the fluidic channel 150 and the catheter (FIGS. 5C and 5D) or any suitable location. The flow control system may additionally and/or alternatively use pressure drops, vents, or any suitable technique for controlling fluid flow among the fluidic channels and catheter. The flow control system may also be present in an embodiment that includes only one fluidic channel 150. In another variation, the first and second fluidic channels preferably fluidically communicate with a catheter with dual lumens, such that one catheter lumen is coupled to the first fluidic channel and another catheter lumen is coupled to a second fluidic channel. In yet another variation, the first and second fluidic channels fluidically communicate with separate catheters. Additional variations expand on these variations with three or more fluidic channels.

As best shown in FIG. 3, the frame 110 preferably operates in a folded configuration 114 in which the catheter hub 120 and stabilization hub 130 may be coupled to one another and in an unfolded configuration 116 in which the first and second anchoring points are distributed around the insertion site. To facilitate a folded configuration, the frame 110 preferably allows the catheter hub 120 and stabilization hub 130 to move relative to one another with a significant number of degrees of freedom. In particular, the frame is preferably reversibly bendable or foldable to fold the catheter and stabilization hubs toward each other, or to pass one of the hubs over and/or under the other hub.

Figure 8A:
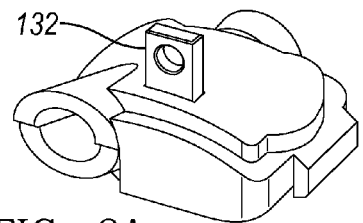
Figure 8B:
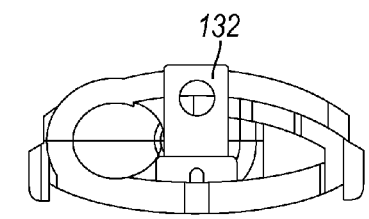

In the folded configuration 114, the catheter hub 120 and stabilization hub 130 may be coupled to one another. With the catheter and stabilization hubs coupled, the hubs experience the same movement relative to a needle 104 being passed into the catheter hub 120 and catheter, such as during insertion of the catheter in the patient. In a first variation, the catheter hub 120 and stabilization hub 130 may be coupled to one another by interaction of the needle 104 with the catheter hub 120 and/or stabilization hub 130. In one example of this variation, as shown in FIGS. 7A-7D, the stabilization hub 130 includes an extension 132, and the catheter hub 120 may include a slot 128 or other recess that receives the extension 132, although in another example the catheter hub 120 may include the extension 132 and the stabilization hub 130 may include the slot 120. The extension 132 defines a through hole 134, such that when the extension 132 is inserted into the slot 128, the through hole 134 is substantially aligned with a needle-receiving channel 124 of the catheter hub 120. In this variation, the frame 110 may be folded into the folded configuration during catheter insertion into the patient by a user (e.g. medical practitioner) who couples the catheter and stabilization hubs together by passing the needle 104 through the channel 124 of the catheter hub 120 and through the through hole 134 of the extension 132. Alternatively, the frame 110 may be folded and/or the needle 104 may be passed through the extension and slot of the hubs during manufacturing, such as during assembly and/or packaging. When the needle 104 is withdrawn from the hubs, the hubs may be decoupled and the frame 110 may be unfolded into the unfolded configuration. As shown in FIGS. 8A and 8B, the extension 132 may be retractable into the hub when the extension is no longer needed, such as when the frame 110 is in the unfolded configuration and ready for securement to the patient. The catheter hub and stabilization hub may include one, two, or any suitable number of extensions and/or slots. However, the catheter hub 120 and/or stabilization hub 130 may additionally and/or alternatively interact with the needle in any suitable manner (e.g., with a housing that surrounds the needle) to facilitate selective coupling of the catheter and stabilization hubs.

Figure 9:
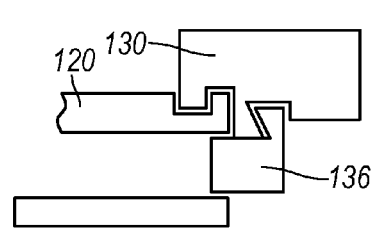
Figure 10:
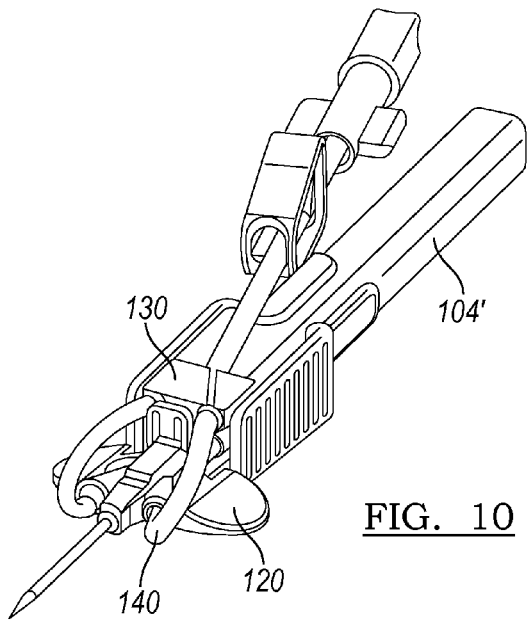
Figure 11A:
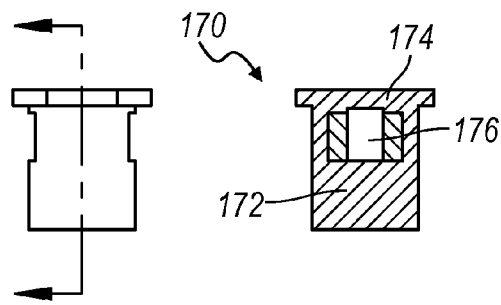
Figure 11B:
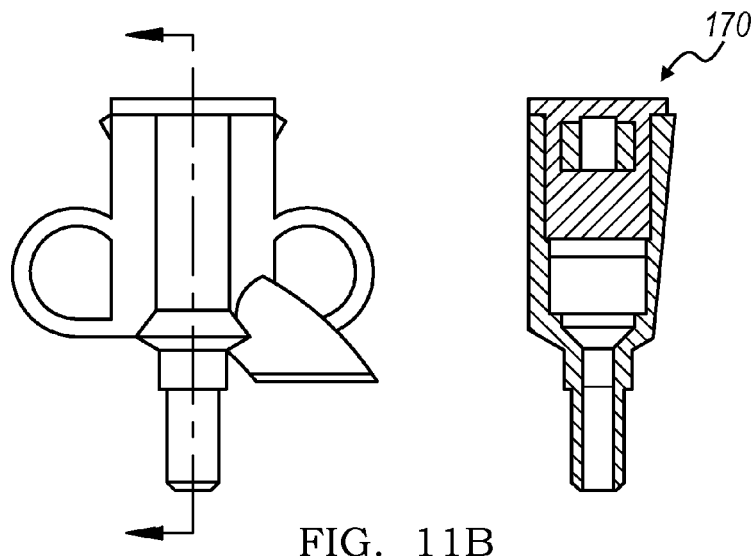
Figure 11C:
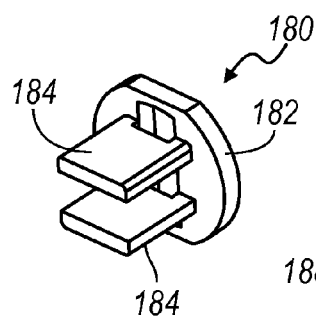
Figure 11D:
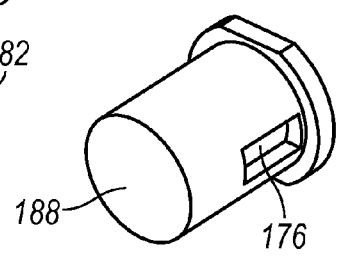
Figure 11E:
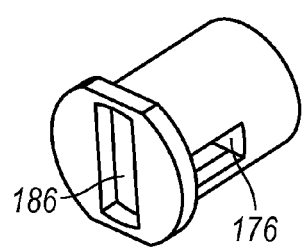

In a second variation, the catheter hub 120 and stabilization hub 130 may be coupled to one another by mutually interacting a third structural element. For example, as shown in FIG. 9, a block 136 may couple to both the catheter hub 120 and the stabilization hub 130 when the frame 110 is in the folded configuration. Although the block 136 is shown in FIG. 9 to have a particular geometry, the block may include a switch, latch, plug, and/or any suitable fastener or other mechanism. Removal of the block 136 may facilitate the decoupling of the catheter hub 120 and stabilization hub, such that frame may be in the unfolded configuration. As another example, as shown in FIG. 10, a needle or needle system 104' may couple to both the catheter hub 120 and the stabilization hub 130 when the frame is in the folded configuration, such as during catheter insertion. Following catheter insertion, removal of the needle system 104' may facilitate the decoupling of the catheter hub 120 and stabilization hub.

In a second variation, the catheter hub 120 and stabilization hub 130 may be coupled to one another in a slidable manner. For example, one of the hubs may have side grooves or channels, and the other hub may have side ridges that slidingly engage with the grooves of the other hub when the frame 110 is in the folded configuration. Other examples of this variation may include tabs inserted into slots, or any suitable mechanism.

In a third variation, the catheter hub 120 and stabilization hub 130 may be coupled to one another with snaps, latches, magnets, and/or any suitable fastener when the frame 110 is folded into the folded configuration. The fastener may be a separate piece that is mutually coupled to the catheter and stabilization hubs. Additional variations of the coupling of the catheter hub and stabilization hub include various combinations of the above variations. Furthermore, the catheter hub and stabilization hub may be coupled in any suitable manner, with or without the cooperation of the needle to help secure or lock the coupling of the catheter hub and stabilization hub.

In the unfolded configuration 116, as shown in FIGS. 1A and 1B, the catheter hub 120 and stabilization hub 130 are decoupled such that the frame 110 may be secured to the patient such that the first and second anchoring points 112 and 112' are distributed around the insertion site 102 of the catheter, thereby stabilizing the catheter. The frame 110 is preferably secured to the patient by securing the catheter hub 120 and stabilization hub 130 to the patient at the first and second anchoring points, respectively. However, the frame 110 may additionally and/or alternatively be secured by securing only the catheter hub 120, only the stabilization hub 130, the lateral members 140 and/or any suitable portion of the frame 110. The frame may alternatively stabilize the catheter at anchoring points located at any suitable locations relative to the catheter insertion site. The frame 110, when secured to the patient, enables the integrated vascular delivery system to stabilize the catheter more effectively than conventional catheter securement devices that stabilize the catheter on only one side of the insertion site, because stabilizing the catheter on two different sides of the insertion site reduces pivoting motions of the catheter that may occur during normal patient movement and/or caregiver manipulates of the IV setup. The frame 110 is preferably secured to the patient with tape, but may additionally and/or alternatively be secured with an adhesive located on the underside of the catheter hub and/or stabilization hub; an elastic strap; a strap fastened with fasteners such as hooks, hook and loop, or magnets; or any suitable securement mechanism.

In one alternative embodiment, as shown in FIG. 6A-6C, the frame 110 includes one catheter hub, two stabilization hubs located on an opposite side of the frame as the catheter hub, two lateral members each connecting the catheter and a respective stabilization hub, and a fluidic channel. In this variation, each hub provides a respective anchoring point, such that the overall frame 110 includes three anchoring points 112, 112' and 112". In other examples, the frame may include any suitable number of anchoring points distributed equally or unequally around the insertion site 102. As shown in FIG. 6A, the catheter hub 120, stabilization hubs 130, and lateral members 140 may be integrated in a single piece. The single piece may include a single kind of material, or may include a rigid core of a first material (e.g. a rigid material such as plastic) and an outer layer of a second material (e.g. soft material such as silicone) covering the rigid core.

Other variations of catheter hub, stabilization hub, and lateral member configurations may be similar to that described in U.S. application Ser. No. 12/855,013 entitled "Integrated vascular delivery system", which is incorporated in its entirety by this reference. Furthermore, the frame may include a catheter hub and a stabilization hub, but lack a lateral member; for example, the catheter hub and stabilization hub may be coupled together in a hinged manner such that the frame can operate in folded ("closed hinge") and unfolded ("open hinge") configurations.

Integrated Vascular Delivery System—Septum

The catheter hub 120 preferably further includes a septum 170 that functions to seal the internal channel 124 of the catheter hub 120 after withdrawal of the insertion needle 104 after catheter insertion, to prevent escape or leakage of blood and other potential biohazards or other fluids from the catheter hub 120. The septum 170 is preferably coupled to the catheter hub 120, preferably disposed within an internal channel 124 of the catheter hub, and may be concentrically aligned with the catheter. The septum 170 is preferably coupled to the catheter hub 120 and includes a primary seal 172 and a secondary seal 174. The primary seal 172 is an inner seal that functions as a first defense against fluid escaping, and the secondary seal 174 is an outer seal that functions as a second defense against fluid escaping. In some embodiments, the septum 170 may include fewer or more seals similar to the primary and secondary seals, which may be suitable for some applications to modify the amount of fluid leakage protection. The septum preferably defines a cavity 176 between the primary and secondary seals that may contain trapped fluid that passes through the primary seal. The cavity 176 may be larger than the diameter of the needle 104 to reduce frictional force on the needle during needle insertion through the septum, thereby increasing the ease of passing the needle through the septum. However, the cavity may alternatively be closely fit, and/or may include a material with a lower friction coefficient and/or fluid absorbent material.

The septum 170 may include an elastomeric material, and may have a diameter slightly larger than the channel 124 within the catheter hub 120, such that compression of the septum 170, when assembled in the channel, seals the annular gap between the outer circumferential edges of the septum and the walls of the channel within the catheter hub 120, thereby preventing fluid from escaping through the annular gap, and further maintaining the coupling between the septum 170 and the catheter hub 120, similar to a press fit. The septum 170 may additionally and/or alternatively include a sealant material applied to the outer edges of the septum to prevent passage of fluid between the septum and catheter hub walls, and/or be temporarily or permanently bonded to the catheter hub such as with sonic welding, chemical welding, or adhesive.

As shown in FIGS. 11A-11E, in a preferred embodiment, the septum 170 includes a rigid core 180 and a compressible plug 188 coupled to the rigid core. The rigid core is a framework that preferably includes a back wall 182 with aperture 186 and wall members 184 extending from the ball wall. The back wall 182 may provide a flange that helps seat the septum 170 within the catheter hub 120. The wall members 184 are preferably substantially parallel, but may be in any suitable relative orientation that defines a gap between the wall members. The compressible plug 188 is coupled partially or wholly around the rigid core, covering or filling the aperture 186 and surrounding the wall members 184 to define a cavity 176 in a central portion of the septum. One end of the compressible plug forms the primary seal 172, and the other end of the compressible plug covering the aperture of the back wall forms the secondary seal 174. The aperture 186 of the back wall allows needle puncture access in and out of the septum cavity (and the catheter). The rigid core 180 is preferably made of a rigid plastic such as polycarbonate, acrylonitrile butadiene styrene (ABS) or other styrene, and the compressible plug 188 preferably includes an elastomeric material such as isoprene or silicone. However, the rigid core and compressible plug may include any suitable materials. The compressible plug is preferably coupled to the rigid core in an overmolding manufacturing process, but may additionally and/or alternatively include other coupling mechanisms or processes such as adhesive.

In a first alternative variation, as shown in FIGS. 12A-12C, the septum is a split septum 270 that includes a split 272 along a portion of its length. The split longitudinally divides the septum into approximately two halves or other multiple portions. The split may terminate near the inner face of the primary seal 172, such that the split 272 travels along at least half of the length of the septum and is joined near the primary seal, but the split may alternatively be any suitable length, including along the entire length of the septum such that the septum includes two separate portions. As shown in FIG. 12C, when the septum 270 is assembled into the catheter hub 120, the channel of the catheter hub preferably radially compresses the septum material to close the split, thereby forming the cavity 176 and the secondary seal 174. The split septum may be manufactured through injection molding, such as with a mold having a cavity complementary to the septum shape as shown in FIG. 12B. In another example of this variation, the split may begin at the inner primary seal and continue towards the secondary seal. In yet another example of this variation, the septum may be split longitudinally along two or more lines, forming three or more split portions.

In a second alternative variation, as shown in FIGS. 13A and 13B, the septum is a dual grommet septum 370 that includes at least two septum pieces 372 or "grommets" placed serially within the catheter hub 120. One of the septum pieces forms the primary seal 172 and another septum piece forms the secondary seal 174. The septum pieces 372 are preferably immediately adjacent to each other such that part of their interior faces are contacting and form a fluid-tight seal against the catheter hub wall. The interior faces of the septum pieces 372 may be chamfered or radiused to define the septum cavity 176 between the septum pieces, but the septum pieces may alternatively have any suitable geometry. Alternatively, the septum pieces may be separated by a distance, such that the septum cavity is at least partially formed by the walls of the catheter hub 120. In other examples of this variation, the septum may includes three or more septum pieces placed serially within the catheter hub 120, such as to provide three or more seals.

In a third alternative variation, as shown in FIGS. 14A and 14B, the septum 470 includes at least two separate septum pieces 472 and an inner sleeve 474 disposed between the septum pieces. In this variation, two septum pieces are placed serially within the catheter hub 120, either directly adjacent to each other or separated by a distance. One of the septum pieces forms the primary seal 172 and another septum piece forms the secondary seal 174. The interior faces of the septum pieces 472 are preferably adapted to receive the inner sleeve 474, such as by defining axially aligned recesses. The inner sleeve 474 may be cylindrical and sized to fit within the recesses of the septum pieces, with an inner diameter large enough to form a cavity 176 that accommodates the diameter of the needle 104. The inner sleeve 474 is preferably rigid, and made of a thermoplastic material or any other suitable rigid material, although the inner sleeve may be made of any suitable material. In other examples of this variation, the septum may include more than two septum pieces, such as further including an outer sleeve-like septum part surrounding the inner sleeve.

Figure 15A:
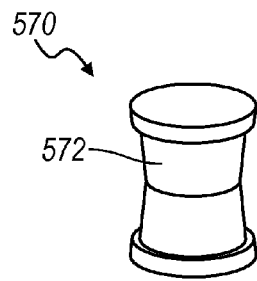
Figure 15B:
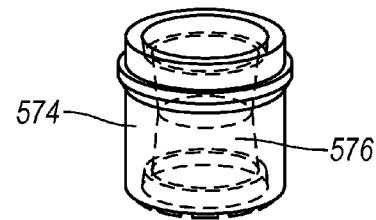
Figure 15C:
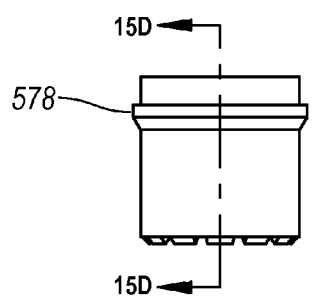
Figure 15D:
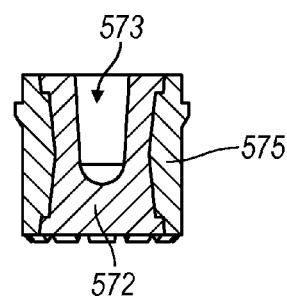
Figure 15E:
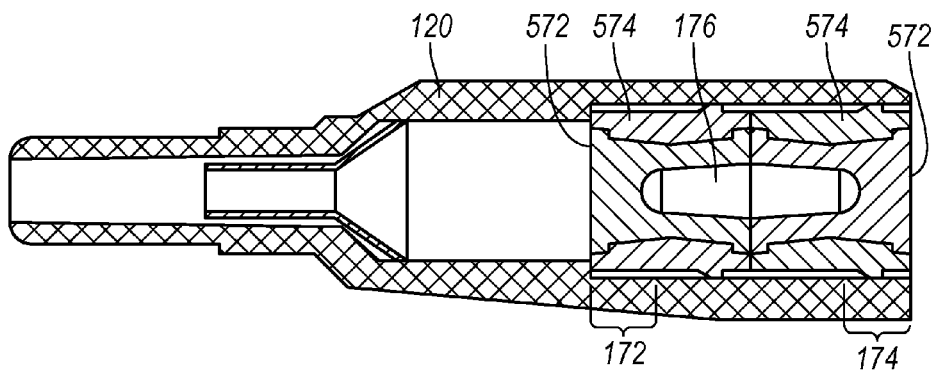

In a fourth alternative variation, as shown in FIGS. 15A-15E, the septum 570 includes a housing with first and second housing portions 574 and first and second septum pieces 572. In this variation, as shown in FIG. 15E, the septum includes a distal half and a proximal half that is substantially a mirrored version of the distal half, with each half including a housing portion 574 and a corresponding septum piece 572. As shown in FIGS. 15A and 15B, each housing piece includes a tapered, hourglass-shaped chamber 576 for receiving a corresponding septum piece. The taper in the chamber 576 helps reduce relative movement such as translational movement between the septum piece 572 and the housing 574. Each housing piece may further include an external annular flange or other protrusion that helps reduce translational movement between the housing and the catheter hub 120. The two housing pieces 574 may be coupled together and/or to the catheter hub 120 through ultrasonic welding, epoxy or other adhesive, threads, and/or any suitable coupling mechanism. As shown in FIGS. 15C and 15D, each septum piece 572 preferably includes a cavity 573 that extends inward from one open end of the septum piece, and the septum pieces are preferably assembled such that the open ends of the septum pieces abut against each other. In this manner, the closed ends of the septum pieces form primary and secondary seals 172 and 174, respectively, of the septum 570, and the joined open ends of the septum pieces form enclosed septum cavity 176. The housing and septum pieces are preferably combined, with a corresponding septum portion nested within (e.g. molded into or pressed into) each housing portion, and the combined housing and septum pieces are preferably mounted within the catheter hub 120.

Figure 16A:
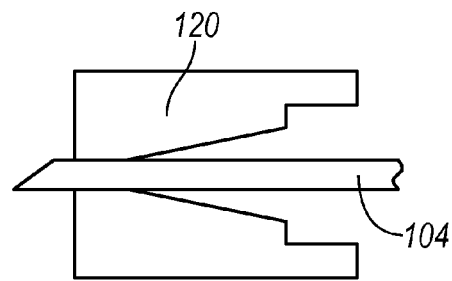
Figure 16B:
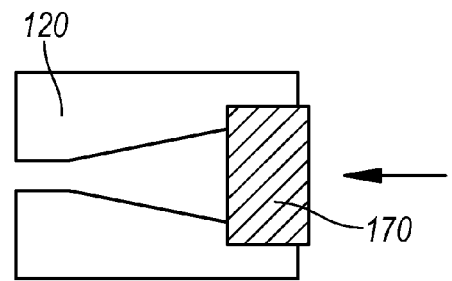
Figure 17A:
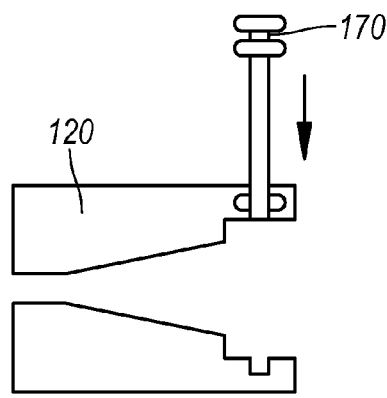
Figure 17B:
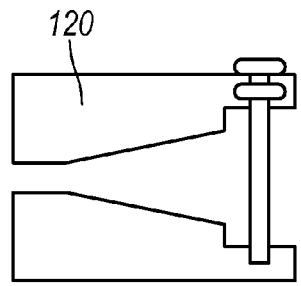
Figure 18A:
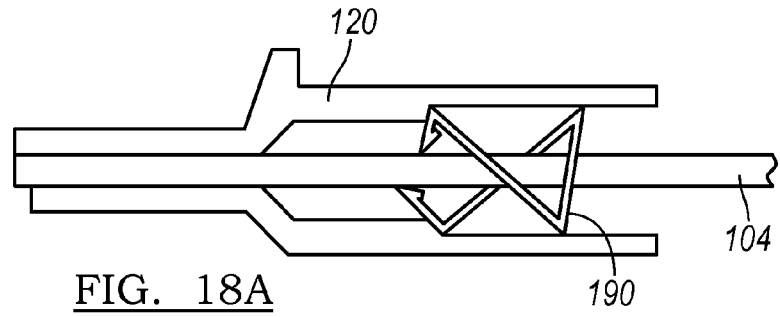
FIGS. 18-23 are schematics of variations of the needle shield in the integrated vascular delivery system of a preferred embodiment.
Figure 18B:
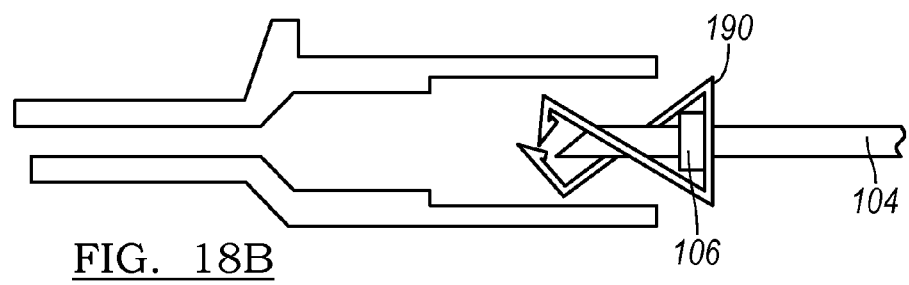
Figure 19A:
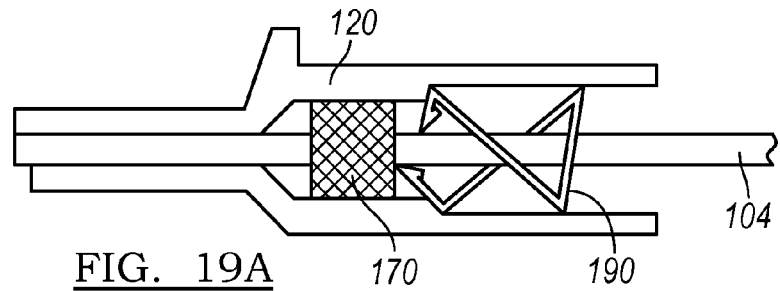
Figure 19B:
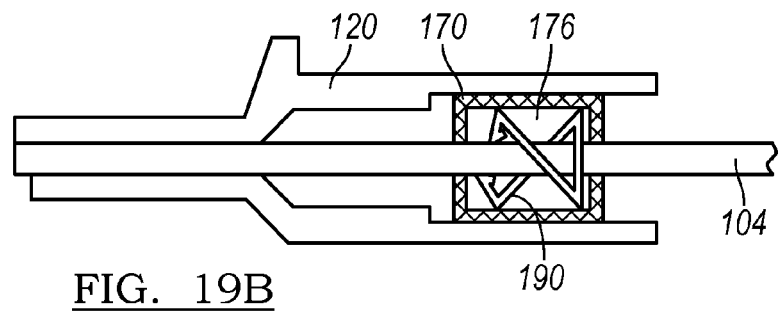

In an alternative embodiment, the septum may have only a primary seal. In a first alternative variation of this embodiment, the septum 170 is made of a flexible material that self-seals to form a hermetic seal on the hub. This self-sealing septum prevents fluid from passing out of the catheter hub 120, contributing to a closed system in which blood and other fluids will not exit the catheter hub. In a second alternative variation, as shown in FIGS. 16 and 17, the septum 170 may be sealed with a plug, such as a stopper or sealant material applied to the septum by a user. Before and during catheter insertion the back end of the channel of the catheter hub may be left open (FIGS. 16A and 17A). After the catheter is inserted in the patient, the user may occlude the blood vessel (such as by applying external direct pressure), withdraw the needle 104 from the catheter and catheter hub 120, place a plug on the back end of the catheter hub 120 to prevent fluid flow out of the hub (FIGS. 16B and 17B), and allow the blood vessel to be in fluid communication with the catheter (such as by releasing external direct pressure on the blood vessel). The plug may include a separate stopped plug applied to the catheter hub (FIG. 16), a sliding piece that the user slides to gate off the back of the hub (FIG. 17), a hinged piece that the user swings to the back of the hub, and/or any suitable septum piece. Any of these single seal variations of the septum may be repeated serially to form two seals (primary and secondary) or more seals.

The septum may be one or more of the embodiments and variations described above, and/or one or more of the embodiments described in U.S. Provisional Applications 61/346,292 filed 19 MAY 2010 and 61/407,797 filed 28 OCT. 2010, which is each incorporated in its entirety by this reference. Furthermore, the septum may be any suitable mechanism that helps prevent escape or leakage of fluid from the catheter hub 120.

Integrated Vascular Delivery System—Needle Shield

As shown in FIGS. 18-23, the catheter hub 120 and/or stabilization hub 130 may include a needle shield 190. The needle shield 190 functions to blunt, or protect the user from, the distal end of the needle 104 after the needle is withdrawn from the catheter and catheter hub after catheter insertion. The needle shield 190 helps prevent accidental needle sticks to the user and the transfer of biological hazards. The needle shield 190 is preferably coupled to the catheter hub 120 and/or stabilization hub 130, but may additionally and/or alternatively be coupled to any suitable portion of the system. The needle shield 190 is preferably a clip such as a spring clip, but may alternatively include any suitable blunting mechanism such as a cap. In general, during insertion of the catheter into the patient, the needle 104 passes through an inactive needle shield 190 and into the catheter (e.g., FIG. 18A). After the catheter is placed in the patient, the needle 104 is withdrawn from the catheter in a proximal direction and engages with the needle shield 190, such as due to interaction with a needle catch 106 on the needle 104. After the needle catch 106 engages with the needle shield, the needle shield is triggered to decouple from the catheter hub and/or stabilization hub and cover or blunt the distal end of the needle (e.g., FIG. 18B). The now active needle shield 190 continues to cover the distal end of the needle 104 as the needle is further withdrawn and removed from the catheter hub 120. The needle catch 106 that triggers decoupling of the needle shield 190 from the hub may be one or more of several variations. In one variation, the needle catch 106 may be an annular structure around the needle body that catches on a portion of the needle shield 190 as the needle is withdrawn from the hub. In another variation, the needle catch 106 may include barbs that allow free passage of the needle through the needle shield 190 when the needle passes into the catheter hub 120, but catch on the needle shield 190 when the needle withdraws from the catheter hub 120. Alternatively, the needle catch 106 may be located on the needle shield 190. However, any suitable variation of the needle catch 106 that facilitates the engagement of the needle and the needle shield 190, and the disengagement of the needle shield from the hub, may be used.

Figure 20:
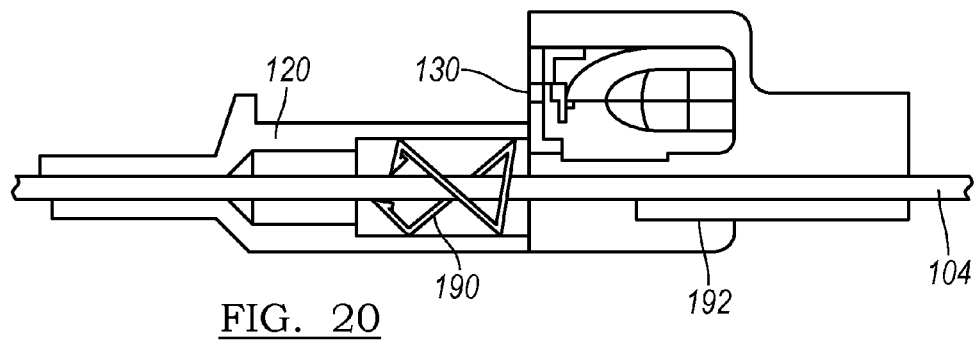

The needle shield 190 may be configured in one or more of several arrangements. In a first embodiment, the needle shield 190 is coupled to the catheter hub 120. In a first variation of this first embodiment, the needle shield is removably coupled to an internal portion of the catheter hub 120. For example, the needle shield 190 may be coupled to an internal surface of a proximal portion of the catheter hub 120 (FIGS. 18 and 20), a distal portion of the catheter hub 120 or any suitable internal surface of the catheter hub. As shown in FIG. 18, the needle shield 190 may be coupled to an internal surface of the catheter hub recessed within the catheter hub, or as shown in FIG. 20, the needle shield 190 may be coupled to an internal surface of the catheter hub approximately flush with an external surface of the catheter hub, such as adjacent to the stabilization hub when the frame is in the folded configuration. As another example, the needle shield 190 may be engaged within the catheter hub 120 proximal to the septum 170 (FIG. 19A), and/or distal to the septum 170. As another example, the needle shield is engaged within the septum 170 of the catheter hub (FIG. 19B), such as within the cavity, a slit, or other suitable receptacle within the septum. As yet another example, the needle shield 190 may be adjacent to a flash chamber 192.

Figure 21A:
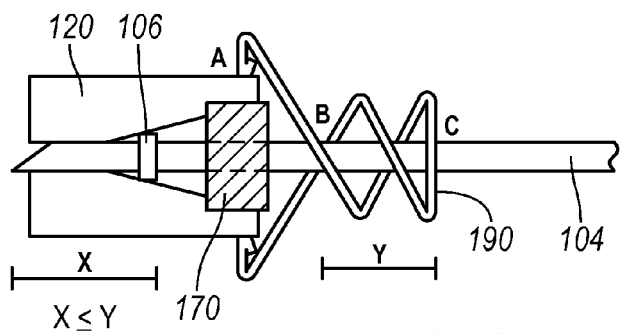
Figure 21B:
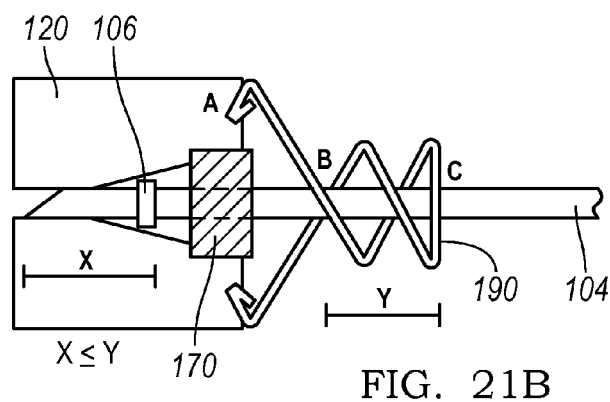

In a second variation of the first embodiment, the needle shield 190 is removably coupled to an external portion of the catheter hub 120. For example, as shown in FIGS. 21A and 21B, the needle shield may interact with the catheter hub 120 and/or the needle 104 at least three points. The needle shield may couple to the catheter hub 120 at a first point a, such as to the outside of the hub (e.g., FIG. 21A) or to notches or other receiving features on the proximal portion of the catheter hub 120 (e.g., FIG. 21B). The needle shield 190 closes around the distal end of the needle 104 at a second point b. The withdrawal of the needle 104 causes disengagement of the needle shield from the catheter hub when needle catch 106 engages the needle shield 190 at a third point c. In this example, the needle shield may be a spring clip configured such that when the needle catch 106 on the needle 104 engages with the needle shield during withdrawal, the engagement simultaneously triggers containment of the needle tip at point b and the disengagement of the needle shield from the catheter hub. The spring clip is preferably dimensioned relative to the needle such that a distance "x", defined as the distance between the distal end of the needle 104 and the needle catch 106, is approximately equal to or less than distance "y", defined as the distance between points b and c, although the spring clip may have any suitable geometry. However, the needle shield may be any suitable mechanism to blunt the needle tip outside the catheter hub.

Figure 22A:
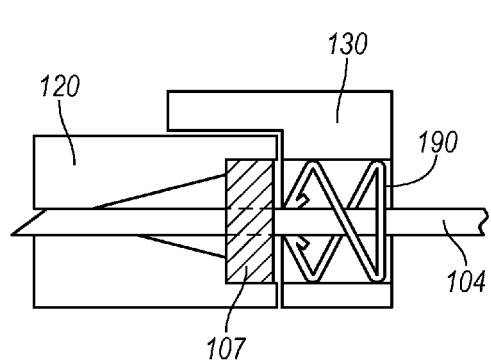
Figure 22B:
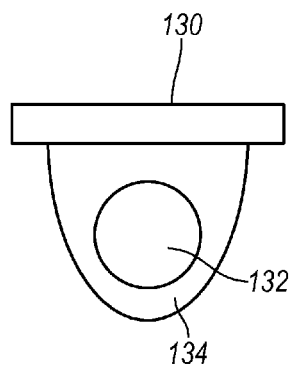

In a second embodiment, the needle shield 190 is coupled to the stabilization hub 130. In a first variation of this embodiment, as shown in FIGS. 22A and 22B, the needle shield is removably coupled to an internal portion of the stabilization hub, in a manner similar to that of the first embodiment. For example, the stabilization hub may include a tab that substantially aligns with the catheter hub 120 when the frame 110 is in the folded configuration. The tab may define a recess to which an internal needle shield couples, or an external needle shield may be externally coupled to the tab. During catheter placement, the frame 110 is preferably in the folded configuration and the needle 104 passes through the tab, through the needle shield, and through the catheter hub 120. Upon removal of the needle 104 from the catheter hub 120, the needle shield disengages from the stabilization hub 130 and covers the needle. Following withdrawal of the needle from the catheter hub and disengagement of the needle shield from the stabilization hub, the frame 110 may be unfolded into its unfolded configuration. In a second variation, the needle shield 190 is removably coupled to an external portion of the stabilization hub, particularly when the frame 110 is in the folded configuration, similar to the variation in which the needle shield is coupled to an external portion of the catheter hub.

Figure 23:
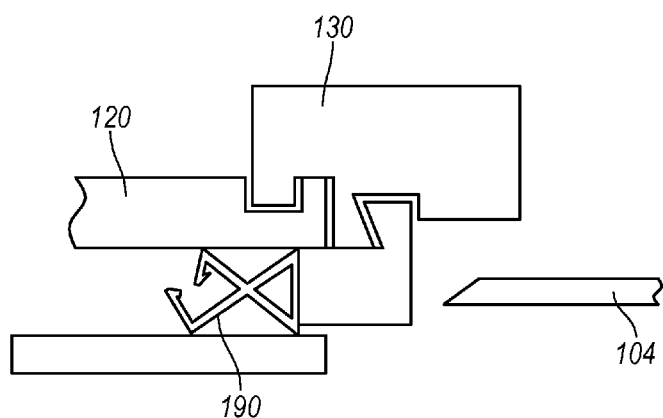
Figure 24:
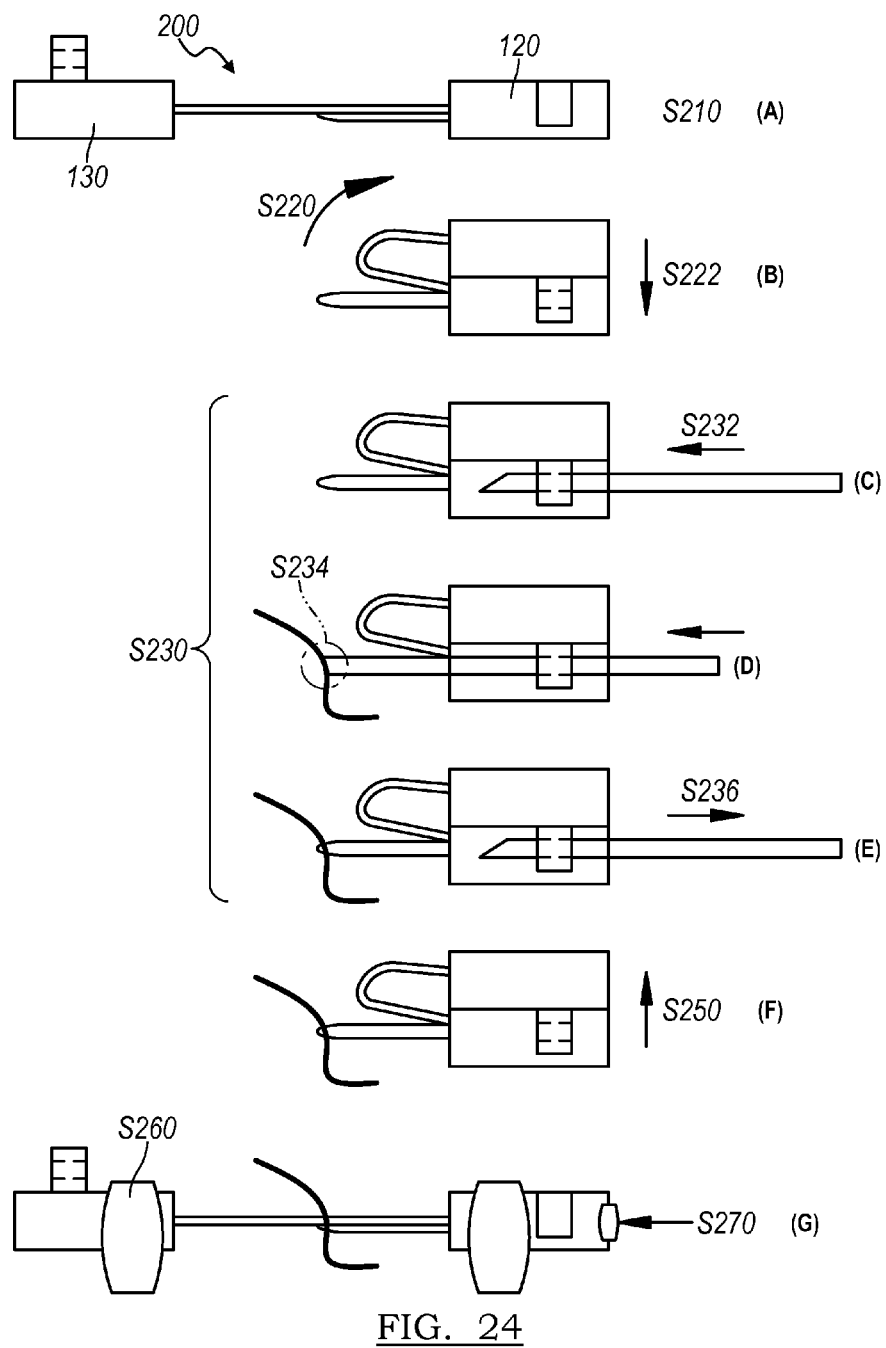
FIGS. 24-27 are schematics of the method of using an integrated vascular delivery system of a preferred embodiment.
Figure 25:
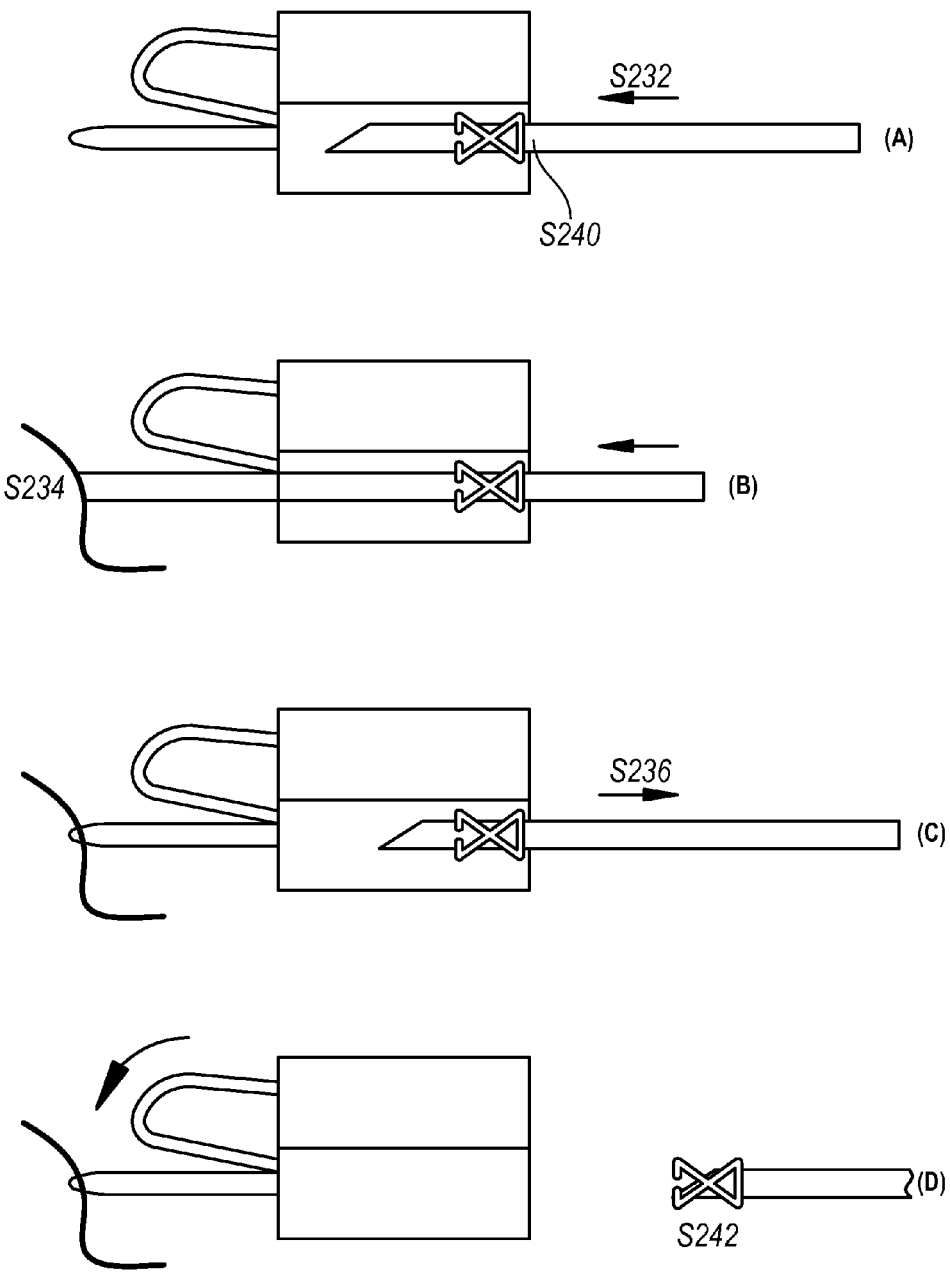

Additional alternative embodiments of the needle shield include various combinations of the above variations of the needle shield. In other words, the needle shield may be inside and/or outside the catheter hub 120 and/or stabilization hub. For example, as shown in FIG. 23, the needle shield 190 may be coupled directly to an internal portion of the catheter hub 120 and indirectly to an external portion of stabilization hub 130. As another example, the needle shield may be partially inside and partially outside the catheter hub, or the three-point contact needle shield of the first embodiment may be coupled to the stabilization hub instead of the catheter hub 120. Further, the needle shield of any of these variations may be coupled to a sheath that covers at least a portion of the needle body, such that the needle blunter and sheath combination contains more than solely the distal end of the needle.

The needle shield may be one or more of the embodiments and variations described above, and/or one or more of the embodiments described in U.S. Provisional Applications 61/418,358 filed 30 NOV. 2010, 61/438,782 filed 2 FEB. 2011, and 61/448,318 filed 2 MAR. 2011, which are each incorporated in its entirety by this reference. Furthermore, the needle shield may be any suitable mechanism that sufficiently covers and/or blunts the distal end of the needle.

Method for Using an Integrated Vascular Delivery System

As shown in FIGS. 24-27, a method 200 for using an integrated vascular delivery system on a patient includes the steps of: providing a frame S210, wherein the frame includes a catheter hub that receives a catheter, and a stabilization hub; folding the catheter hub and stabilization hub towards one another S220, thereby folding the frame into a folded configuration; coupling the catheter hub and stabilization hub to one another S222; inserting the catheter into the patient at an insertion site S230; unfolding the frame such that the frame surrounds the insertion site in an unfolded configuration S250; and securing the frame to the patient at a plurality of anchoring points distributed around the insertion site S260, thereby stabilizing the catheter relative to the insertion site.

As shown in FIG. 24A, the step of providing a frame S210 preferably includes providing an integrated vascular delivery system similar to that described above, although any suitable frame with a catheter hub and stabilization hub may be used. For example, a suitable integrated vascular delivery system may include a frame with a catheter hub and a stabilization hub coupled together with a hinged joint. Furthermore, the integrated vascular delivery system may include fewer hubs.

The step of folding the catheter hub and stabilization hub towards one another S220 functions to expose the end of the catheter, which may help provide visual and/or physical clearance for the catheter to be positioned at an insertion site. As shown in FIG. 24B, folding the catheter hub and stabilization hub towards one another thereby folds the frame into a folded configuration. The folding step S220 may include passing the stabilization hub towards a relatively stationary catheter hub, passing the catheter hub towards a relatively stationary stabilization hub, or simultaneously passing both the catheter and stabilization hubs towards each other. In one example of the folding step S220, the stabilization hub is positioned to be a proximal portion of the frame (relative to the patient) and the catheter hub is positioned to be a distal portion of the frame. Relative to an insertion site on the forearm of a patient, the stabilization hub is closer to the elbow and the catheter hub is closer to the hand. In this example, the folding step S220 folds the stabilization hub away from the patient towards the catheter hub. Alternatively, the frame may be folded and/or the needle may be inserted into the catheter prior to use such as during manufacturing (e.g. during assembly or packaging). In alternative embodiments, the catheter hub and stabilization hub may be moved in any suitable relative motion, such as sliding or twisting relative to each other.

The step of coupling the catheter hub and stabilization hub to one another S222 functions to secure the frame in the folded configuration. As shown in FIG. 24B, coupling the catheter hub and stabilization hub S222 may include inserting a portion of one of the catheter and stabilization hubs into the other of the catheter and stabilization hubs. For example, inserting a portion of one of the hubs may include inserting an extension of at least one of the hubs into a slot or other recess of another hub. However, in other variations, coupling the catheter hub and stabilization hub may include engaging the hubs in a slidable manner, activating a latch, or any suitable coupling mechanism.

Inserting the catheter into the patient at an insertion site S230 functions to establish a conduit through which fluid can be administered to or transferred from the patient. As shown in FIG. 24C-E, inserting the catheter S230 preferably includes inserting a needle into the catheter hub, passing the needle telescopically through the catheter, penetrating the insertion site with the needle, positioning the catheter within the insertion site S234, and withdrawing the needle from the catheter S236. In one variation, inserting the needle into the catheter hub includes passing the needle through the extension S232 (the extension of one of the hubs received by another hub in step S222), thereby locking the catheter and stabilization hubs.

In one variation, as shown in FIGS. 25A-D, inserting the catheter S230 may further include engaging at least a distal portion of the needle with a needle shield S240 coupled to the catheter hub and/or stabilization hub. The needle shield preferably functions to cover the distal end of the needle and may a spring clip, cap, or any suitable mechanism. The needle shield may be inside or outside the catheter hub, inside or outside the stabilization hub, or coupled to any suitable part of the frame. In this variation, inserting the catheter may further include decoupling the needle shield S242 from the catheter hub and/or stabilization hub before, simultaneously with, or after, withdrawing the needle from the catheter hub S236. The action of the needle insertion and/or needle withdrawal may trigger the decoupling of the needle shield from the catheter hub and/or stabilization hub. In this manner, the needle may be fully withdrawn from the catheter hub while still being engaged and/or covered with the needle shield.

Unfolding the frame S250 functions to orient the frame around the insertion site in an unfolded configuration. As shown in FIG. 24F, unfolding the frame S250 preferably reverses the movement performed on the catheter hub and stabilization hub in the step of folding the frame S220, but may additionally and/or alternatively include other suitable steps such as moving the catheter hub and stabilization hub in another direction, twisting a portion of the frame, or sliding a portion of the frame.

Figure 26:
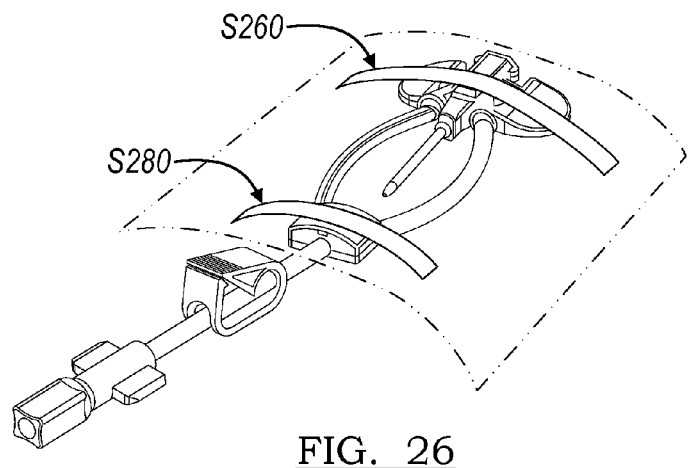
Figure 27:
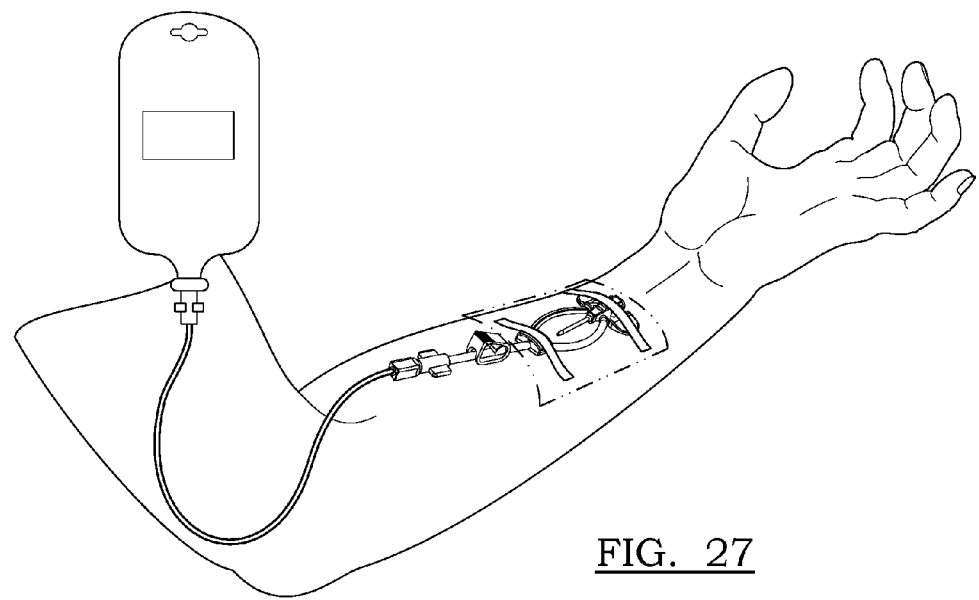

Securing the frame to the patient S260 at a plurality of anchoring points distributed around the insertion site functions to stabilize the frame, and thereby the catheter, relative to the insertion site. Securing the frame includes securing the catheter hub at a first anchoring point and securing the stabilization hub at a second anchoring point. As shown in FIGS. 24G and 26, the first and second anchoring points are distributed around the insertion site, preferably on substantially opposite sides of the insertion site. More preferably, as shown in FIG. 27, one of the anchoring points is proximal to the insertion site and another anchoring point is distal to the insertion site. However, the first and second anchoring points may be distributed around the insertion site in any suitable manner. In one variation, securing the frame may further include securing the frame at a third anchoring point, such that the first, second and third anchoring points are distributed around the insertion site. The frame may also be secured to the patient at four or more anchoring points. The multiple anchoring points may be approximately equally or unequally distributed around the insertion site. The securing steps may include taping the frame to the patient (e.g. with medical tape or sterile adhesive dressing), adhering the frame to the patient with adhesive, strapping the frame to the patient, or any suitable securing mechanism.

As shown in FIG. 24G, the method may further include applying a septum plug S270, preferably to a proximal portion (e.g. needle-receiving channel) of the catheter hub, which functions to help prevent escape or leakage of fluids from the catheter after the catheter insertion. The septum plug may be applied in one or more several manners depending on the nature of the plug, and applying a septum plug S270 may include sliding a septum plug over the catheter hub (e.g. septum is a sliding gate), stopping a channel in the catheter hub (e.g. septum is a stopper), or any suitable steps.

As shown in FIG. 26, the method may further include the step of applying a dressing over the insertion site and the frame S280. The step of applying a dressing functions to protect the insertion site against bacteria, viruses, and other pathogens. The dressing is preferably a breathable, sterile dressing. The dressing is preferably transparent to allow visualization of the insertion site, and includes adhesive to attach to the skin of the patient and to provide securement of the frame. The dressing can be used after the frame has been secured to the patient, or the dressing can be used to secure the frame to the patient. However, the dressing can include any suitable device or method to assist in the protection of the insertion site.

As a person skilled in the art will recognize from the previous detailed description and from the figures and claims, modifications and changes can be made to the preferred embodiments of the invention without departing from the scope of this invention defined in the following claims.

We claim:

1. An integrated vascular delivery system adapted to be placed on a patient, comprising:
    a frame including:
        a catheter hub providing a first anchoring point on the patient, wherein the catheter hub is configured to receive a catheter insertable in a patient to transfer a fluid at an insertion site;
        a stabilization hub coupled to the catheter hub and providing a second anchoring point on the patient;
        wherein the frame operates in a folded configuration wherein the catheter hub is configured to reversibly couple to the stabilization hub, and an unfolded configuration wherein the first and second anchoring points are distributed around the insertion site to anchor the frame to the patient, thereby stabilizing the catheter;
    a fluidic channel extending between the catheter hub and the stabilization hub, that fluidically communicates with the catheter; and
    a needle shield, coupled to at least one of the catheter hub and stabilization hub, that allows a needle to penetrate the catheter, through the needle shield, in an inactive configuration and that covers a distal end of the needle in an active configuration, in withdrawing of the needle from the catheter, wherein the needle is configured to facilitate insertion of the catheter into the patient.

2. The system of claim 1, wherein one of the catheter hub and stabilization hub includes an extension, wherein in the folded configuration of the frame, the extension is inserted in the other one of the catheter and stabilization hubs.

3. The system of claim 1, wherein in the unfolded configuration of the frame, one of the first and second anchoring points is proximal to the insertion site and the other one of the first and second anchoring points is distal to the insertion site, relative to the patient.

4. The system of claim 3, wherein in the unfolded configuration of the frame, the first anchoring point is substantially opposite the second anchoring point.

5. The system of claim 1, wherein the fluidic channel is at least partially housed within a lateral member extending between the catheter hub and the stabilization hub.

6. The system of claim 5, further comprising a second lateral member extending between the catheter hub and the stabilization hub.

7. The system of claim 6, wherein the first and second lateral members are substantially nonparallel.

8. The system of claim 1, wherein the fluidic channel includes a turnabout portion in which fluid flows in a direction different from that within the catheter.

9. The system of claim 8, wherein the turnabout portion of the fluidic channel is configured to direct fluid flow in a direction substantially opposite from that within the catheter.

10. The system of claim 8, wherein the turnabout portion of the fluidic channel is fixed within at least one of the catheter hub and stabilization hub.

11. The system of claim 1, wherein the needle shield is removably coupled to the catheter hub, and configured to engage a needle catch, upon withdrawal of the needle from the catheter hub, that transitions the needle shield from the inactive configuration to the active configuration.

12. The system of claim 11, wherein the needle shield is removably coupled to an internal portion of the catheter hub.

13. The system of claim 1, wherein the needle shield is removably coupled to the stabilization hub.

14. The system of claim 1, wherein the needle shield includes a spring clip that engages a distal portion of the needle upon withdrawal of the needle from the catheter in the active configuration of the needle shield.

15. The system of claim 1, further comprising a catheter that is coupled to the catheter hub.

16. The system of claim 1, further comprising a septum coupled to the catheter hub.

17. The system of claim 16, wherein the septum includes a primary seal and a secondary seal.

18. The system of claim 16, wherein the septum includes a rigid core.

19. The system of claim 18, wherein the septum further includes an elastomeric plug surrounding at least a portion of the core.

20. The system of claim 19, wherein the rigid core includes a wall defining an aperture, and a plurality of members extending from the wall.

21. The system of claim 20, wherein the elastomeric plug surrounds the plurality of members to define a septum cavity between the members.

22. The system of claim 17, wherein the septum includes a hollow, rigid septum housing and a tapered elastomeric plug disposed within the rigid septum housing.

23. The system of claim 17, wherein the septum includes a cavity and a spring clip disposed inside the cavity.

24. The system of claim 1, wherein at least one of hubs includes a sensor that measures a biometric or fluid parameter.

25. An integrated vascular delivery system adapted to be placed on a patient, comprising:
    a frame including:
        a catheter hub providing a first anchoring point on the patient, wherein the catheter hub is configured to receive a catheter insertable in a patient to transfer a fluid at an insertion site; and
        a stabilization hub coupled to the catheter hub and providing a second anchoring point on the patient;
    a fluidic channel extending between the catheter and the stabilization hub, that fluidically communicates with the catheter;
    a needle shield, coupled to at least one of the catheter hub and stabilization hub, that allows a needle to penetrate the catheter, through the needle shield, in an inactive configuration and covers a distal end of the needle in an active configuration, in withdrawing of the needle from the catheter;

wherein the frame operates in:
a folded configuration wherein the catheter and stabilization hubs are coupleable; and
an unfolded configuration wherein the first and second anchoring points are distributed around the insertion site to anchor the frame to the patient, thereby stabilizing the catheter.

26. The system of claim 25, wherein one of the catheter and stabilization hubs includes an extension, wherein in the folded configuration of the frame, the extension is inserted in the other one of the catheter and stabilization hubs.

27. The system of claim 26, wherein the stabilization hub includes an extension with a through hole that receives a needle when the frame is in the folded configuration.

28. The system of claim 27, wherein the extension is retractable.

29. The system of 27, wherein in the unfolded configuration of the frame, one of the first and second anchoring points is proximal to the insertion site and the other one of the first and second anchoring points is distal to the insertion site, relative to the patient.

30. The system of 29, wherein in the unfolded configuration of the frame, the first anchoring point is substantially opposite the second anchoring point across the insertion site.

31. The system of claim 25, further comprising a first flexible lateral member configured to house at least a portion of the fluidic channel and a second flexible lateral member.

32. The system of claim 31, wherein the first and second flexible lateral member are substantially non-parallel.

33. The system of claim 25, wherein the fluidic channel includes a turnabout portion in which fluid flows in a direction different from that within the catheter.

34. The system of claim 33, wherein the turnabout portion of the fluidic channel directions fluid flow in a direction substantially opposite from that within the catheter.

35. The system of claim 33, wherein the turnabout portion of the fluidic channel is fixed within at least one of the catheter and stabilization hubs.

36. The system of claim 25, wherein the needle shield is removably coupled to the catheter hub.

37. The system of claim 36, wherein the needle shield includes a spring clip that engages a distal portion of the needle.

38. The system of claim 25, further comprising a catheter that is coupled to the catheter hub.

39. The system of claim 25, further comprising a septum coupled to the catheter hub.

40. The system of claim 39, wherein the septum includes an elastomeric plug.

41. The system of claim 39, wherein the septum includes a primary seal and a secondary seal.

42. The system of claim 41, wherein the septum further includes a rigid core.

43. The system of claim 42, wherein the septum further includes an elastomeric plug surrounding at least a portion of the core.

44. The system of claim 43, wherein the rigid core includes a wall defining an aperture, and a plurality of members extending from the wall.

45. The system of claim 44, wherein the elastomeric plug surrounds the plurality of members to define a septum cavity between the members.

46. The system of claim 39, wherein the septum includes a hollow, rigid septum housing and a tapered elastomeric plug disposed within the rigid septum housing.

47. The system of claim 39, wherein the septum includes a cavity and a spring clip disposed inside the cavity.

48. The system of claim 25, wherein at least one of hubs includes a sensor that measures a biometric or fluid parameter.

49. An integrated vascular delivery system adapted to be placed on a patient, comprising:
a frame including:
a catheter hub providing a first anchoring point on the patient, wherein the catheter hub is configured to receive a catheter insertable in the patient to transfer a fluid at an insertion site; and
a stabilization hub providing a second anchoring point on the patient;
wherein the frame operates in:
a folded configuration wherein the catheter and stabilization hubs are coupleable; and
an unfolded configuration wherein the first and second anchoring points are distributed around the insertion site to anchor the frame to the patient, thereby stabilizing the catheter.

50. An integrated vascular delivery system adapted to be placed on a patient, comprising:
a frame including:
a catheter hub providing a first anchoring point on the patient, wherein the catheter hub is configured to receive a catheter insertable in the patient to transfer a fluid at an insertion site; and
a stabilization hub providing a second anchoring point on the patient; and
a septum disposed in the catheter hub and including:
a rigid core having a core wall defining an aperture and a plurality of members extending from the core; and
an elastomeric plug circumferentially surrounding at least a portion of the plurality of members and defining a septum cavity;
wherein the frame operates in:
a folded configuration wherein the catheter and stabilization hubs are coupleable; and
an unfolded configuration wherein the first and second anchoring points are distributed around the insertion site to anchor the frame to the patient, thereby stabilizing the catheter.

51. The system of claim 27, wherein the needle has a lumen.

52. The system of claim 29, wherein the needle has a lumen.

53. The system of claim 2, wherein the extension defines a through hole configured to allow passage of the needle into the catheter, and wherein passage of the needle into the through hole reversibly locks the frame in the folded configuration.

* * * * *